US009260687B2

(12) United States Patent
Skill

(10) Patent No.: US 9,260,687 B2
(45) Date of Patent: Feb. 16, 2016

(54) APPARATUS FOR TREATMENT OF FLUID STREAMS AND METHOD OF CONDUCTING SAME

(76) Inventor: Steven Skill, Plymouth (GB)

(*) Notice: Subject to any disclaimer, the term of this patent is extended or adjusted under 35 U.S.C. 154(b) by 744 days.

(21) Appl. No.: 13/147,148

(22) PCT Filed: Jan. 27, 2010

(86) PCT No.: PCT/GB2010/000113
§ 371 (c)(1),
(2), (4) Date: Aug. 2, 2011

(87) PCT Pub. No.: WO2010/086589
PCT Pub. Date: Aug. 5, 2010

(65) Prior Publication Data
US 2011/0278219 A1    Nov. 17, 2011

(30) Foreign Application Priority Data
Jan. 30, 2009   (GB) .................................. 0901565.2

(51) Int. Cl.
*C12M 1/06*     (2006.01)
*C12M 1/00*     (2006.01)
*C12M 1/12*     (2006.01)

(52) U.S. Cl.
CPC ............... *C12M 27/06* (2013.01); *C12M 21/02* (2013.01); *C12M 23/06* (2013.01); *Y02W 10/37* (2015.05)

(58) Field of Classification Search
CPC ....... C12M 21/02; C12M 27/06; C12M 23/06
See application file for complete search history.

(56) References Cited

U.S. PATENT DOCUMENTS 5,496,730 A *   3/1996   Teramachi .................. 435/290.2
5,637,219 A     6/1997   Robinson et al.
(Continued)

FOREIGN PATENT DOCUMENTS

| DE | 3617300 A1 | 11/1986 |
|---|---|---|
| GB | 1549038 A | 7/1979 |
| GB | 2423525 A | 8/2006 |
| KR | 20030018196 A | 3/2003 |

OTHER PUBLICATIONS
International Search Report of PCT/GB2010/000113 dated Mar. 30, 2010, 4 pages.
(Continued)

*Primary Examiner* — Michael Marcheschi
*Assistant Examiner* — Gautam Prakash
(74) *Attorney, Agent, or Firm* — Jason Saunders; Arnold, Knobloch & Saunders, L.L.P.

(57) ABSTRACT

An apparatus for contacting a fluid stream with microorganisms is provided, the apparatus comprising a housing having a contacting chamber therein defined by a wall of the housing; a first inlet for the fluid stream to be treated; a first outlet for removing a liquid culture medium stream containing microorganisms; a rotor assembly comprising an impeller moveable within the contacting chamber to promote contact between the fluid stream being treated and the liquid culture medium within the contacting chamber; wherein at a least a portion of the wall of the housing defining the contacting chamber is transparent to light. A method of treating a fluid stream with microorganisms is also provided, the method comprising contacting the fluid stream with the microorganisms in a contacting zone, the microorganisms being retained in a liquid phase, wherein contact of the fluid stream with the microorganisms is enhanced by the action of a moving impeller, the contacting zone being within a housing, at least a portion of which is transparent to the passage of light.

11 Claims, 13 Drawing Sheets

(56) References Cited

U.S. PATENT DOCUMENTS 5,958,761 A 9/1999 Yogev et al.
6,287,852 B1 * 9/2001 Kondo et al. ............. 435/292.1
6,370,815 B1 4/2002 Skill et al.
2008/0182325 A1 7/2008 Hobbs et al.

OTHER PUBLICATIONS

Written Opinion of PCT/GB2010/000113 dated Mar. 30, 2010, 5 pages.

* cited by examiner

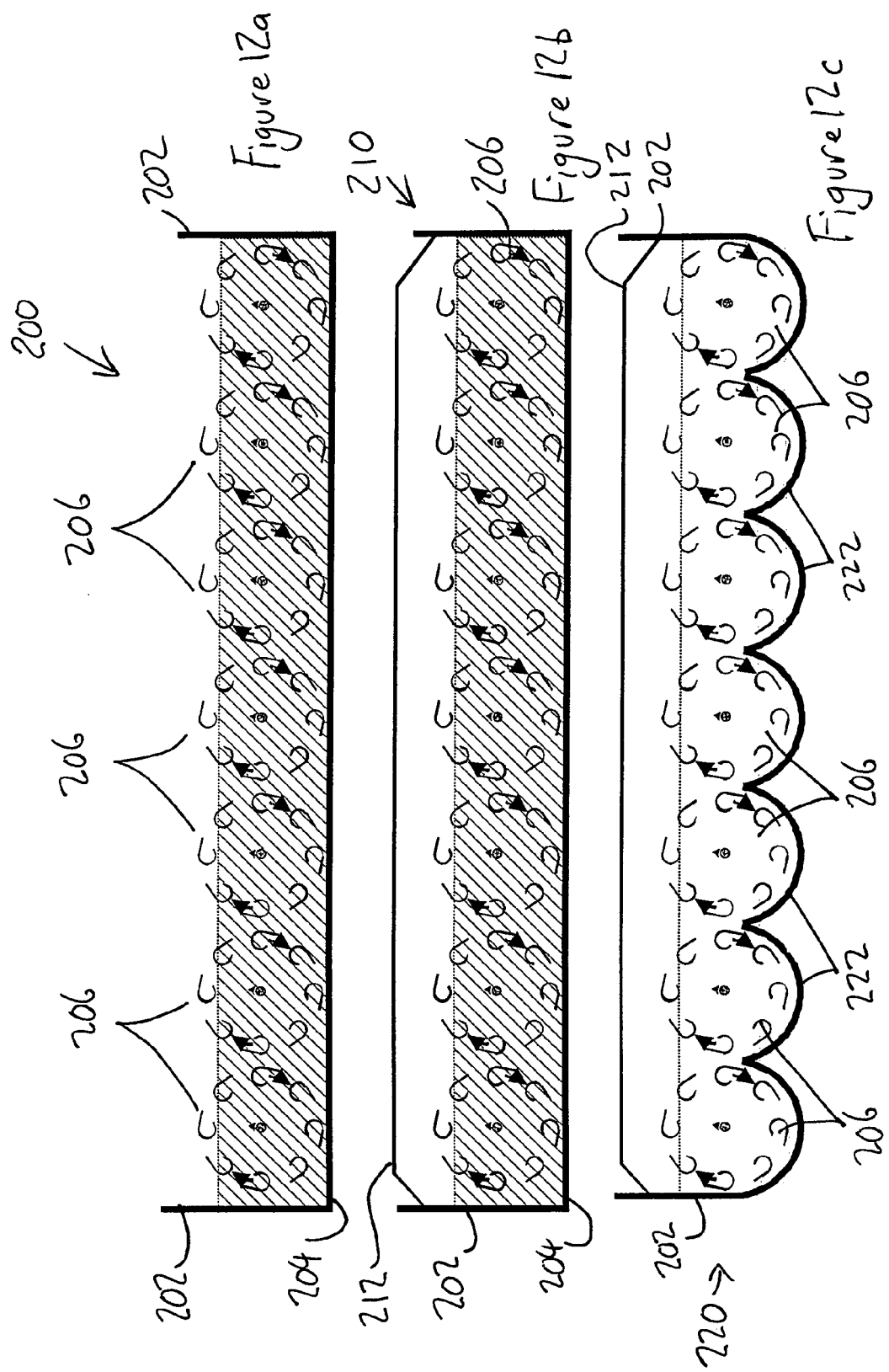

APPARATUS FOR TREATMENT OF FLUID STREAMS AND METHOD OF CONDUCTING SAME

BACKGROUND OF THE INVENTION

The present invention is concerned with an apparatus for the treatment of fluid streams. The apparatus finds general application in the removal and/or conversion of components of fluid streams. In one particular aspect, the present invention is concerned with the treatment of waste streams, for example sequestering carbon dioxide from waste streams such as flue gases and the like. The invention further relates to methods of conducting the same.

BRIEF SUMMARY OF THE INVENTION

Many processes produce waste liquid and/or gas streams. In the past, such streams have been emitted into the environment, perhaps with some processing to reduce their impact on the environment. More recently, there has been growing concern regarding such streams and their long term effect on the environment. One example is the amount of carbon dioxide that is being exhausted into the atmosphere by a very wide range of processes. Carbon dioxide has been identified as a so-called 'greenhouse' gas and the observed increase in atmospheric temperatures globally are being attributed to increasing levels of carbon, dioxide in the atmosphere. Carbon dioxide is produced in many processes, perhaps the most significant producer of carbon dioxide being combustion, for example from the combustion of solid, liquid and gaseous carbon-containing fuels to generate power. However, carbon dioxide is just one of a larger number of greenhouse gases, all of which are considered to have detrimental affects on the atmosphere and environment.

As a consequence there is considerable attention being paid to the treatment of waste fluid streams, for example power station flue gases and the like, to remove carbon dioxide and other environmentally unacceptable components. One proposal for the treatment of such waste fluid streams is to use micro-organisms to treat the waste streams and remove the unwanted components. This treatment generates biomass as the normal product of the biological processes of the micro-organisms, which in turn may be used to produce valuable primary and secondary metabolites, including biofuel feedstocks, using non-fermentative processes. A general summary of some aspects of this concept is provided by Dimitrov, K. 'GreenFuel Technologies: A Case Study for Industrial Photosynthetic Energy Capture'. March 2007, Brisbane, Australia.

The use of micro-organisms to process organic materials is well known in the art and is used on a commercial scale in an increasing number of applications. Accordingly, there is considerable prior art relating to bioreactors and other apparatus for contacting micro-organisms with materials to be treated, processed or consumed. In the case of treating waste fluid streams to remove hazardous components and to harvest the resulting biomass for processing into valuable primary and secondary metabolites, any apparatus or system must be efficient both in contacting the micro-organisms with the stream to be treated and in allowing the micro-organisms to be collected.

The purification of contaminated water using micro-organisms is described in WO 2004/046037. There is disclosed an apparatus composing a water permeable matrix of a transparent or translucent substrate and a bio-film comprising one or more photosynthetic micro-organisms on the substrate. The bio-film is a layer of colonies of the micro-organisms formed on the matrix of the substrate. The bio-film is described as being slimy, due to the secretion of polysaccharides by the microorganisms. While micro-organisms may act to treat the water, this form of apparatus is limited in its applications to a gaseous waste stream. Further, the collection and harvesting of the micro-organisms is difficult, presenting a problem when the biomass is to be converted into a biofuel or the like. U.S. Pat. No. 6,370,815 discloses a reactor for growing photosynthetic microorganisms, the micro-organisms being grown in a tube having a gas inlet at one and a gas outlet at the other end. The tube contains a rotor with vanes extending therefrom to wipe the inner surface of the tube. The tube is disposed in a bath containing a liquid at an angle to the horizontal, such that the end of the tube with the gas inlet is lowermost A photosynthetic bioreactor is disclosed in WO 98/24879 and has a plurality of parallel passageways for housing the micro-organisms. The passageways are formed with walls transparent to light. The micro-organisms are held in a liquid suspension that is pumped at a low flow rate through the passageways. A pump with flexible vanes is employed, to reduce the level of shear to which the micro-organisms are subjected. Similar varied pumps are disclosed in GB 2 341 896 and US 2001/0002976.

An apparatus for the continuous digestion of organic matter is disclosed in U.S. Pat. No. 5,637,219. The apparatus comprises a generally cylindrical vessel, in which is mounted a rotatable rotor assembly. The rotor assembly comprises two or more plate members extending around a common central axis and disposed to divide the interior of the vessel into three or more compartments. A plurality of buckets extend between adjacent plate members and rotate therewith. Such an apparatus is available commercially for a wide range of applications and is known as the Graesser Contactor™. U.S. Pat. No. 5,637,219 describes the use of the contactor in the anaerobic digestion of organic materials using micro-organisms. The contactor is used to process waste liquid streams or liquid-and-solid streams. The liquid streams, with or without entrained solids, are fed to the contactor and contacted with the microorganisms held in suspension in a liquid phase. Rotation of the plate members and associated buckets ensures a high degree of contact between the micro-organisms and the liquid being treated.

One form of reactor for contacting fluid streams to be processed with a microorganism is a photobioreactor, that is a reactor in which the microorganisms employed are phototrohpic and rely upon or use light from a suitable source to efficiently carry out their metabolic processes. A general overview of photobioreactor technology is provided by Tredici, M. R., 'Bioreactors, Photo', in Flickinger, M. C. and Drew, S. W. (ed.), 'Encyclopedia of Bioprocess Technology: Fermentation, Biocatalysis and Bioseparation', vol. 1. Wiley, New York (1999), pages 395 to 419.

2008/178739 discloses a photobioreactor for use in the treatment of gases, such as flue gases, and for the production of biomass. The bioreactor disclosed is for use in the treatment of gases containing elevated concentrations of carbon dioxide. The photobioreactor comprises an elongated vessel having a cover that is transparent to light. The elongated vessel may have one or more photobioreactor sections. In the case that a plurality of photobioreactor sections are employed, the sections are preferably interconnected, each section having an inlet and outlet. A single transparent cover may be provided to extend over a plurality of separate bioreactor sections.

GB 2,423,525 is concerned with a photobioreactor for use in a solvent extraction process for the production of biolipids. The reactor comprises a combination of a plug flow reactor and an oscillatory flow reactor, in which biolipids produced by microorganisms are removed by extraction with a suitable solvent. The biolipids are subsequently recovered from the solvent for use in the production of biodiesel. The plug flow reactor portion comprises a pipe having a transparent wall, through which light may enter the pipe.

WO 2007/098150 is directed to photobioreactors and their uses. The photobioreactors comprise a container having walls that are at least partially transparent to the passage of light therethrough. The container is divided into a plurality of sections, with the adjacent sections being in fluid communication. Inlet and outlet ports are provided in the container for the provision and removal of fluids. The bioreactors are provided with means to aerate the fluid contents of the containers and the microorganisms within them. Means for regulating the temperature of the fluid within the containers is also provided.

JP 5344879 discloses a bioreactor for the culture of microorganisms. The bioreactor comprises a generally cylindrical vessel arranged horizontally, the vessel being transparent to the passage of light. The vessel is supported on rollers, which are rotated, to in turn rotate the vessel about its longitudinal axis. Agitating blades are provided in the vessel. The use of rollers and a rotating vessel render the arrangement of JP 5344879 particularly complex and very difficult to employ on a large scale.

US 2007/0214899 is concerned with sampling ports and related container systems, in particular for use with bioreactor systems. There is disclosed therein a bioreactor system comprising a container supported with a housing. The container held within the housing may be flexible or rigid and may be transparent or opaque. A mixer is provided within the container to mix and/or suspend fluid within the container.

Other examples of photobioreactors are disclosed in U.S. Pat. No. 5,614,378, U.S. Pat. No. 4,952,511, U.S. Pat. No. 5,137,828 and U.S. Pat. No. 4,676,956. In many of the reactors disclosed light is provided to a culture medium within the reactor using one or more radiators or light sources located within the reactor itself. The location of the light sources or radiators within the bioreactor has generally been required in order to provide light to all regions of the culture medium, as the penetration of light from the surface of the liquid medium is severely limited and extends to only a very shallow depth.

A method and apparatus for treating waste streams using photosynthetic microorganisms is disclosed in U.S. Pat. No. 6,416,993.

From a review of the known methods and apparatus for processing fluid streams, there is a need for an improved apparatus to function as a bioreactor. In particular, there is a need for an improved apparatus that can efficiently treat waste gaseous streams, in particular flue gases produced by the combustion of fuels in power plants and the like. There is an especial need for an efficient system for treating such flue gases to remove carbon dioxide. It would be most advantageous if the system could be operated with the flue gas at substantially the same pressure as it is produced by the power plant or the like, that is without the need for significant, or more preferably any, compression. It would be a further significant advantage if the bioreactor could employ phototrophic microorganisms without the need to rely upon an artificial light source and/or complex arrangements for conveying sunlight into the body of the liquid culture medium.

According to a first aspect of the present invention there is provided an apparatus for contacting a fluid stream with microorganisms, the apparatus comprising:
    a housing having a contacting chamber therein defined by a wall of the housing; a first inlet for the fluid stream to be treated:
    a first outlet for removing a liquid culture medium stream containing microorganisms;
    a rotor assembly comprising an impeller moveable within the contacting chamber to promote contact between the fluid stream being treated and the liquid culture medium within the contacting chamber;
    wherein at a least a portion of the wall of the housing defining the contacting chamber is transparent to light.

The apparatus of the first aspect of the present invention provides an efficient means for contacting a fluid stream to be processed with a liquid medium containing microorganisms. The microorganisms are most preferably contained in the liquid medium in the form of a suspension. However, other means for retaining microorganisms is a liquid phase, such as holding the microorganisms in a transparent matrix, for example as described in WO 2004/046037, may also be employed.

The apparatus may be used to carrying out a wide range of treatments or processing of components in a fluid stream by the microorganisms in the liquid medium. The processing may comprise the conversion of one or more components from the fluid stream being treated into biomass, for subsequent harvesting and use. Alternatively, or in addition, the processing may comprise the conversion of one or more components in the fluid stream being treated into other, desirable components by the microorganisms. In such a case, the components produced in this way may be expressed or excreted by the microorganisms into the liquid medium for removal, for example by known extraction techniques, such as solvent extraction, distillation or the like. Alternatively, the components produced in this way may be retained within the cells of the microorganisms and recovered from the cells in known manner once the microorganisms have been harvested and removed from the apparatus.

In particular, the apparatus is most suitable for the processing of a gaseous stream, especially a flue gas. The apparatus is most advantageous in the processing of a gaseous stream, such as flue gas or the like, to remove carbon dioxide and/or other substances, before the fluid stream is emitted to the atmosphere or reused in another beneficial process. In this way, a gaseous stream such as flue gas or the like may have its carbon dioxide content converted into biomass, allowing the treated gas to be emitted to the atmosphere with reduced carbon emissions or used in other processes, while also allowing the biomass to be recovered and used, for example as a feedstock in the manufacture of valuable primary and secondary metabolites, such as biofuel feedstocks and phytopharmaceuticals.

The apparatus comprises a housing. The housing may be any suitable shape or configuration. A particularly preferred arrangement is one in which the housing is cylindrical, as the construction and handling of cylindrical vessels is well known. The housing contains a contacting chamber therein defined by a wall of the housing. The contacting chamber may be any suitable shape or configuration. However, the contacting chamber is preferably cylindrical, formed by the wall of the cylindrical housing.

The housing may be positioned in any suitable orientation. Preferably, the housing is arranged with its longitudinal axis horizontal. This arrangement is particular advantageous, as it allows a flow regime to be established in an elongate vessel in which the fluid stream to be processed is contacted with the microorganisms in the liquid medium. The apparatus may comprise a single housing, in which is arranged one or more contacting chambers. In one preferred arrangement, the apparatus is constructed on a modular basis, with a plurality of housings arranged to receive a fluid stream to be processed. The plurality of housings may be arranged in series to receive the fluid stream being processed in a sequential manner. Alternatively, the plurality of housings may be arranged in a parallel manner, such that the fluid stream being processed is divided between two or more of the housings. In one preferred embodiment, the housing is provided as one or more elongate cylindrical or tubular housings arranged horizontally, as will be described hereinafter.

The housing may comprise a single contacting chamber or a plurality of such chambers. In one arrangement, the housing contains a plurality of contacting chambers with adjacent chambers being separated by a partition extending across the interior of the housing. The fluid stream to be processed may be introduced into each contacting chamber sequentially. Alternatively, the fluid stream to be processed may divided among the plurality of contacting chambers within the housing.

When the apparatus of the present invention is in use, a liquid medium containing microorganisms, typically in suspension, is contacted with the fluid stream to be processed. The liquid medium is most typically an aqueous medium. The microorganisms are phototrophic organisms and require a source of light of sufficient intensity in order for their normal metabolic processes to proceed. Accordingly, in order to allow the microorganisms to process the fluid stream to be treated, light is required within the contacting chamber. To provide the requisite light, at least a portion of the housing is transparent to light, allowing light to enter the contacting chamber. In this respect, the term 'transparent' is a reference to the material of the housing being such as to allow the passage of sufficient light of the appropriate range of wavelengths through the wall of the housing to ensure efficient propagation of the microorganisms within the contacting chamber. In one embodiment, the entire housing is transparent to light. In the case that the housing has only a portion that is transparent, it will be understood that the housing must be oriented when installed and in use in order to ensure light may enter through the transparent portion.

One or more portions of the housing or components within the housing may be provided with a reflective or mirrored surface, in order to reflect incident light within the housing, thereby increasing the efficiency of contacting the microorganisms with the light entering the housing. In particular, if the housing comprises only a portion that is transparent and allowing the passage of light into the housing, the inner wall of the housing opposing the transparent portion may be reflective or mirrored.

The apparatus of the present invention is particularly suitable for using natural light to irradiate the microorganisms within the contacting chambers. When intended for use with natural light, the size and orientation of the transparent portion of the housing will be determined by the geographic location of the apparatus when in use and the orientation of the apparatus with respect to the sun. The optimum orientation of the apparatus, in particular the housing, will be readily determinable by the person skilled in the art for a given location.

In the case that the apparatus is to employ natural light, means for providing an artificial light source may also be provided either to supplement the natural radiation from the sun, as may be required, or to allow operation to continue during the hours of darkness. The means for providing artificial light may be provided external to the housing, such that the articificially produced radiation is incident on the transparent portion of the housing. Alternatively, the means for producing artificial light may be disposed within the housing, for example within the or each contacting chamber. Suitable assemblies for providing artificial light within the housing will be apparent to the person skilled in the art and known in the art.

The housing of the apparatus may be constructed from a variety of materials. Examples of suitable materials for providing the transparent portion of the housing include polymers, such as polyethylene, polypropylene, polyurethane, polycarbonate, polyvinylpyrrolidone, polyvinylchloride, polystyrene, poly(ethylene terephthalate), poly(ethylene naphthalate), poly(1,4-cyclohexane dimethylene terephthalate), polyolefin, polybutylene, polyacrylate, poly(methyl methacrylate) and polyvinlyidene chloride, per-fluoro plastics, Perspex, PTFE and PET. Other suitable materials include soda glass, borosilicate glass, and quartz glass. The material of the housing does not have to be rigid. Rather, the housing may also consist of a thin wall of material, such as polyethylene, supported by a rigid support frame creating a substantially rigid structure, for example a substantially cylindrical housing. The rigid support frame must be arranged to allow sufficient light to reach and pass through the housing, for example by comprising supporting members sufficiently spaced apart to allow the passage of light therebetween and/or by having components that are partly or wholly transparent to the passage of light.

The apparatus comprises an inlet for the fluid stream to be processed. This may be a gaseous stream, a liquid stream or a mixed phase stream. The fluid stream may contain entrained or suspended solid matter or particles. As noted, the apparatus is particularly suitable for the processing of gaseous streams, in particular flue gas. A single inlet may be sufficient in the case that the fluid stream to be processed is a liquid that may be combined directly with the liquid culture medium containing the microorganisms. For example, in the case of the treatment of an aqueous stream, this would readily mix and combine with an aqueous medium containing the microorganisms. A single inlet may also be provided when the apparatus is being used to process a gaseous stream. In this case, the gas to be processed may be introduced into the housing through the inlet and allowed to flow through the contacting area. However, more likely, the apparatus will comprise a second inlet for liquid to be supplied to the contacting chamber to supplement the liquid culture medium containing the microorganisms. In use, the second inlet may also be used to provide fresh microorganisms, nutrients or other components needed to establish and maintain the required microorganism culture in the apparatus. Separate inlets may be provided for one or more such components, if desired.

As noted, the housing comprises an inlet for introducing a gas into the contacting chamber, when the apparatus is being used to process or treat a gaseous stream. In a particularly preferred arrangement, the apparatus is operated to have a first region within the contacting chamber that is occupied by the gas stream being processed and a second region containing the liquid medium in which the microorganisms are suspended. Typically, the first region will be above the second region, with the gas stream passing across the surface of the liquid medium. In such a case, the inlet for the gas stream is preferably arranged to direct the incoming gas directly into the first region. In this way, excessive agitation of the liquid medium and the microorganisms contained therein is minimised. This in turn reduces the shear applied to the microorganisms, which is typically advantageous, as described in more detail below. If liquids are to be introduced into the contacting chamber in addition to the gaseous stream, the inlet for the liquid streams is preferably arranged to direct the incoming liquid directly into the second region of the contacting chamber.

As noted above, the housing of the apparatus may be a suitable vessel, for example a cylindrical vessel, preferably an elongate or tubular vessel having a length that is many times greater than its diameter. Such a tubular vessel is particularly suitable for inclusion in an array of such vessels which may be oriented to capture natural light in the most efficient manner. For example, the tubular vessels may be arranged in a vertical array or stack, with their axes horizontal, the array being oriented to receive the incident light in the most efficient manner throughout the hours of daylight. The array of tubular vessels is also suitable for location on the roof of a building and is particularly adaptable to fit the dimensions and angle of incline of the roof.

In an alternative embodiment, the housing is in the form of a tank or pond. The tank or pond is typically defined by a set of retaining walls. The retaining walls may extend partly or wholly into the ground. In such a case, the tank or pond is provided with a cover extending over the fluid media contained in the tank or pond, with the cover being partly or wholly transparent to the incident natural light.

The apparatus comprises a first outlet for removing the liquid culture medium and microorganisms. In the case that the fluid stream to be processed is completely consumed within the apparatus or can be removed together with the culture medium, a single outlet for all materials within the apparatus may suffice. More preferably, the apparatus comprises a second outlet for removing the remains of the fluid stream being processed. Thus, in the case of the treatment of a flue gas, the apparatus will comprise a first outlet for the unconsumed or unconverted flue gas components, and/or other useful gaseous components produced as metabolites of the microorganisms and a second outlet for the liquid medium containing the microorganisms.

Thus, in the case of the embodiment discussed above, in which the apparatus is to be employed in the treatment or processing of a gaseous stream, such as a flue gas, the housing will comprise an outlet for gas components, including both unconverted gaseous components and any gaseous metabolites, that connects directly with the first region of the contacting chamber. A second outlet for liquid components will be disposed in the housing to allow the direct removal of liquid from the second region within the contacting chamber.

The liquid medium present in the apparatus in use may be a single phase, in particular a single aqueous phase. Alternatively, the apparatus may in use contain more than one liquid phase. In particular, one or more organic liquid phases and an aqueous liquid phase may be present within the contacting chamber, for example in embodiments where components such as metabolites from the microorganisms are removed from the aqueous liquid medium by means of solvent extraction. In such a case, the apparatus may be provided with a plurality of outlets for removing liquid from the housing.

Thus, in the case of the embodiment discussed above, in which the apparatus is to be employed in the treatment or processing of a gaseous stream, such as a flue gas, in operation, three regions may be identified in the contacting chamber. The first region, as described above is occupied by the gaseous stream and is provided with an inlet and an outlet. The second region is occupied by the aqueous liquid medium containing the microorganisms, which is again provided with its respective inlet and outlet. Finally, a third region may be identified, occupied by the immiscible liquid phase, such as an organic solvent. The third region is preferably provided with its own inlet and outlet. Further regions may be present, in the case that the apparatus is operated with three or more immiscible liquid phases.

The apparatus of the present invention is for use with microorganisms that are present and typically contained as a suspension in a liquid, typically an aqueous, medium. The microorganisms are phototrophic and required light to function normally, as noted above. In order to ensure that the fluid stream to be processed is brought into contact with the microorganisms and the microorganisms are exposed to sufficient light, the apparatus comprises a rotor assembly having an impeller moveable within the contacting chamber. The function of the rotor assembly and impeller arrangement is to ensure a high surface area of contact between the liquid medium containing the microorganisms and the fluid stream to be treated. This function is important in the case that the apparatus is used to process a fluid stream, such as a liquid stream, that is immiscible with the liquid medium containing the microorganisms. This function is particularly important in the case of an apparatus being used to treat a gaseous stream, for example a flue gas stream, where a high contact surface area between the gaseous stream and the microorganism-containing medium is required in order to ensure proper and efficient processing of the gas stream. This function is similarly important in the case that the apparatus is operated with a plurality of immiscible liquid phases.

It is preferred that the rotor assembly is arranged to impart only a low amount of energy to the fluid streams, in particular to the liquid media. In this way, the rotation of the rotor assembly consumes less energy. More importantly, the tendency of the rotation of the rotor assembly to cause multiple liquid phases to emulsify is reduced. When two or more liquid phases are present, a rotor assembly that imparts a high amount of energy to the liquid may result in two or more liquid phases combining to form a stable emulsion. In this case, separation of the liquid phases and the components they contain can be a significant processing problem. Accordingly, it is preferred to operate the rotor assembly with only a low energy input to the fluid streams, in particular to avoid emulsification of the liquid streams.

In addition, the rotor assembly and impeller must provide the required high surface area for contact without subjecting the microorganisms to high shears. That is the microorganisms must be provided with a low-shear environment. In order to keep the shear applied to the microorganisms to a minimum, it is not generally possible to intimately mix the gaseous stream to be processed with the liquid phase containing the microorganisms. Rather, in operation, it is typically the case that the contacting chamber will contain a first region or zone containing gas and a second region or zone containing liquid, as discussed above. The rotor assembly is arranged such that the impeller moves from the first region or zone, taking with it the gaseous stream into the second region or zone to contact the liquid medium and suspended microorganisms. A similar principle of operation preferably applies when the apparatus is operated with a plurality of liquid phases present in two or more largely separate regions of the apparatus and the impeller is preferably moved through all the regions, to ensure increased contact between all the fluid phases present in the contacting chamber.

The rotor assembly may consist of any suitable arrangement that is able to move one or more impellers through the fluid media in the contacting chamber and promote mixing of the media, in order to increase the contact between the microorganisms and the fluid stream being processed or treated. Typically, the rotor assembly moves the or each impeller around a closed path within the contacting chamber. In a particularly preferred embodiment, the rotor assembly is arranged to move the or each impeller in a substantially circular motion through the fluid media.

The impeller may be any suitable shape and configuration, provided that it is effective in increasing contact between the fluid being fed to the apparatus and the liquid medium containing the microorganisms. As noted above, the impeller should preferably impart only low energy to the fluids in the contacting chamber, to avoid emulsification of the fluid phases. In the case of an apparatus for the treatment and processing of a gaseous stream, in particular a flue gas, the impeller is effective in increasing and promoting the contact between the liquid medium containing the microorganisms and the gaseous phase within the housing. Similarly, in the case of an apparatus for use in the processing of a liquid stream immiscible with the liquid containing the microorganisms, the impeller will promote contact between the two liquid phases.

Known forms of impeller include paddles, screws, blades and the like. In general, such impellers are operated at high speeds, in turn imparting significant energy to the fluid being mixed. The action of such impellers will generate high shear in a liquid medium, likely to damage microorganisms suspended in the liquid. Accordingly, such known impellers may only be operated at low speeds, in order to reduce the shear generated in the liquid microorganism-containing medium. This in turn may limit their ability to generate the required level of contact between the microorganism-containing liquid medium and the fluid stream being processed. Accordingly, one preferred form of impeller comprises one or more components which, when moved, transport a portion of fluid in one region of the housing to a second region in the housing. For example, a preferred impeller is one that is operable to transport a portion of the microorganism-containing liquid medium into the region of the housing occupied by the fluid stream to be treated and, more preferably, in turn transport fluid from the fluid stream to be treated into the microorganism-containing liquid medium. Such an impeller may be operated at low speeds, thus imparting a low amount of energy to the fluid in the housing and subjecting the microorganisms to only very low levels of shear.

In a particularly preferred arrangement, the liquid containing the microorganisms and the fluid stream to be treated remain in respective regions of the interior of the housing and flow through the housing in their respective regions in a laminar flow regime, with contact between the two phases be promoted solely by the rotor assembly.

The impeller may be an elongate impeller, that is have a length significantly greater than its width or diameter. In one preferred arrangement, the impeller extends substantially the entire length of the contacting chamber in which it is disposed and moved.

A particularly preferred form of impeller is one comprising one or more scoops or buckets, which is moved by the rotor assembly within the contacting chamber in the housing. Such an arrangement is described in U.S. Pat. No. 5,637,219. The impeller of this arrangement is particularly advantageous in that is provides a high level of contact between the various fluid phases, without subject the microorganisms to a high level of shear in the liquid medium. In particular, this arrangement is particularly suitable in contacting a gaseous stream with the liquid microorganism-containing medium. In operation, each scoop or bucket draws a volume of gas into the liquid medium as it passes from the gaseous stream into the liquid phase. The volume of gas is subsequently released as the impeller moves through its arc of rotation in the liquid medium. The gas volume is released as a low number of relatively large bubbles, that return to the gaseous stream as a result of their buoyancy in the liquid phase. The larger diameter bubbles generated in this way, while providing a significant surface area of contact between the microorganisms in the liquid medium and the components in the gas phase, do not impart significant shear to the microorganisms, as would smaller bubbles, for example as generated by spargers and other gas distribution devices.

The scoops or buckets may be of any suitable size and shape. In one preferred embodiment, the scoops or buckets are in the form of elongated troughs extending longitudinally within the housing. The troughs may contain one or more baffles disposed along their length. In general, the size, shape and configuration of the impeller may be selected in order to control the droplet/bubble size when the apparatus is in operation, depending upon the number and nature of the various fluid phases present in the system. Thus, the scoops or buckets, in particular in the form of elongated troughs, may be plain or may be provided with one or more baffles to provide the desired droplet/bubble size in operation.

The rotor assembly may comprise a single impeller. More preferably, the rotor assembly comprises two or more impellers, for example two or more scoops or buckets. When a plurality of impellers is present, they may be arranged to move circumferentially around the longitudinal axis of the housing and pass through substantially the same volume of the housing when rotating. Alternatively, the impellers may be disposed along the longitudinal axis of the housing within the contacting chamber. The rotor assembly may comprise one or more sets of impellers displaced along the longitudinal axis of the contacting chamber, with each set comprising one or more impellers.

In one embodiment, the rotor assembly comprises a shaft extending longitudinally within the contacting chamber, preferably aligned with the longitudinal axis of the contacting chamber and housing, the shaft supporting the one or more impellers present. In such an arrangement, the shaft may be hollow, providing passages for a heat exchange medium, such as liquid or gas, to allow the temperature within the contacting chamber to be regulated and maintained at the optimum temperature for the proper function of the microorganisms.

In operation, microorganisms may tend to grow and collect on the inner surfaces of the contacting chamber and the surfaces of the rotor assembly. As a result, the passage of light into the contacting chamber may be reduced to a level that is unacceptable for efficient growth and functioning of the microorganisms. In addition, components of the fluid streams passing through the contacting chamber may also be deposited on the surfaces within the contacting chamber over time, again reducing the amount of light being provided to the microorganisms. Accordingly, in a preferred embodiment, the apparatus further comprises means to clean the inner surface of the housing within the contacting chamber. Any suitable means may be provided. For example, in one embodiment one or more impellers is provided with means to contact the inner surface of the housing, so as to wipe the inner wall of the contacting chamber. Suitable means include one or more blades, in particular flexible blades, that are held in contact with the inner surface and wipe the inner surface as the impeller is rotated by the rotor assembly.

Alternatively, the apparatus may be provided with one or wiper assemblies that may be moved within the housing, in particular longitudinally within the housing, so as to clean the inner surface of the contacting chamber. The wiper assemblies have means thereon to contact and clean the inner surface of the contacting chamber such as the aforementioned blades. The wiper assembly may be arranged to operate continuously or intermittently, depending upon the rate of growth and deposition of the microorganisms and/or other solid material within the contacting chamber when the apparatus is in use.

In one embodiment, the interior of the housing is divided into a plurality of contacting chambers by a plurality of partitions. Each partition is provided with a wiper assembly at its outer portions so as to contact the inner surface of the housing. Each partition is moveable longitudinally, so as to cause its respective wiper assembly to sweep across and clean a longitudinal portion of the inner surface of the housing. In a particularly preferred arrangement, the partitions are connected to a single, preferably longitudinally extending, actuator, for example a shaft, that may be moved longitudinally within the housing, preferably in a reciprocating manner, thus moving all partitions. The distanced travelled by the partitions is such that the entire inner surface of the housing is swept by the wiper assemblies, when in operation. Most conveniently, the partitions are mounted on the assembly bearing the shaft of the rotor assembly, such that both the partitions and the impellers in each contacting chamber are moveable longitudinally, preferably in a reciprocating motion.

The availability of light to the microorganisms within the contacting chamber will also determine the dimensions of the housing and the contacting chamber. In particular, the housing should be small enough to avoid self-shading of the microorganisms, that is the inability of light to properly penetrate the liquid microorganism-containing medium. This will depend upon the particular microorganisms being employed and the density of the microorganism culture within the contacting chamber, when the apparatus is in use. At higher densities of microorganisms, a smaller housing will be required, in order to ensure that light entering the contacting chamber can penetrate the liquid microorganism-containing medium.

As noted above, in addition to natural light sources, the apparatus may be provided with means providing artificial light to the or each contacting chamber. In one embodiment, the rotor assembly is fabricated from electroluminescent material or provided with arrays of light emitting devices, such as light emitting diodes (LEDs). In addition, or alternatively, light may be introduced into the contacting chamber through a light channeling device, such as a fibre optic cable. Alternatively, or in addition thereto, light may be provided to the microorganisms within the contacting chamber by means of a light emitting rotor assembly, that is a rotor assembly provided with suitable means for emitting light at the required wavelength and intensity directly to the contacting chamber.

To increase the availability of light to the microorganisms within the contacting chamber, components of the rotor assembly may be partly or wholly transparent. In particular, in one embodiment the impellers are of a transparent material, further increasing the access of light to all regions within the contacting chamber.

As noted, the fluid phase or phases within the contacting chamber may contain solid material. For example, the fluid stream being processed may have entrained or suspended therein solid particles. In many cases, such solid material will be inert, that is not take part in the processing reactions and not be significantly affected by the action of the microorganisms. In order to prevent the build up of settled solid material within the contacting chamber, the apparatus may be provided with a means for transporting solid material to an outlet. The solid material may be removed from the contacting chamber through one or more of the outlets for fluid. Alternatively, the solid material may be removed through a dedicated solids-removal outlet. Means for moving and transporting solid material within the contacting chamber are known in the art and include auger-type assemblies having one or more rotatable helical blade or screw assemblies. The means for moving and transporting the solid material within the contacting chamber may have a dedicated drive means, such as a motor and transmission assembly. Alternatively, the means for moving and transporting the sold material may be driven by the same drive means as the rotor assembly, be driven by rotation of the rotor assembly or be mounted so as to rotate with the rotor assembly.

To regulate the temperature within the contacting chamber, the apparatus is preferably providing with a suitable heat exchange system. In the case of the treatment of flue gas, the fluid stream entering the contacting chamber will typically be at an elevated temperature. This may be used as an effective manner of providing heat to the contacting chamber, for example when using thermophilic microorganisms. However, proper regulation of the temperature within the contacting chamber is to be preferred. Accordingly, it preferred that means for regulating and adjusting the temperature within the contacting chamber are preferably provided in the apparatus, in order to ensure that the microorganisms have optimum conditions in the liquid medium for growth and propagation. As noted above, in one embodiment the heat exchange system includes the use of a hollow shaft in the rotor assembly, through which a heat exchange fluid is passed. In addition, or alternatively thereto, the heat exchange system may provide for heat exchange through the wall of the housing. For example, the apparatus may comprise a sprinkler system for spraying water or other coolant onto the exterior of the housing. Other heat exchange means suitable for use in the apparatus will be apparent to the person skilled in the art.

As noted hereinbefore the apparatus of the present invention is suitable for use on a modular basis. Thus, in a further aspect, the present invention provides a system for contacting a fluid stream with microorganisms comprising a plurality of apparatus as hereinbefore described.

Each apparatus will have a rotor assembly as hereinbefore described. Each apparatus may comprise its own dedicated drive system for the rotor assembly. However it is preferred that a plurality of rotor assemblies are driven by a single drive assembly Similarly, while each apparatus may have its own heat exchange system, it is preferred to provide a single heat exchange system to provide the temperature regulation for a plurality of apparatus. In particular, it is preferred to provide a common source of heat exchange medium, for example the supply of heating or cooling liquid through one or more headers.

The plurality of apparatus may be arranged in any suitable pattern or array, for example either in series or in parallel or a combination of the two, in order to achieve the most efficient processing of the fluid stream.

In a further aspect, the present invention provides a method of treating a fluid stream with microorganisms, the method comprising:

contacting the fluid stream with the microorganisms in a contacting zone, the microorganisms being retained in a liquid phase, wherein contact of the fluid stream with the microorganisms is enhanced by the action of a moving impeller, the contacting zone being within a vessel, at least a portion of which is transparent to the passage of light.

The method provides for the treatment of a fluid stream by the action of microorganisms with which the fluid stream is brought into contact. Light is provided to the microorganisms through the transparent portions of the vessel in which the contacting zone is located. The method may be applied to treat a wide range of fluid streams, including both gaseous and liquid streams. The method is particularly suitable for the treatment of gaseous streams, especially gaseous streams containing significant amounts of carbon dioxide, such as flue gas streams and the like. Examples of other gaseous streams that may be treated in this manner include carbon dioxide-containing streams from brewing, biogas generated by anaerobic digestion processes, including biogas generated from refuse and waste in landfill sites, cement kiln exhaust gases and emissions from other fossil fuel combustion processes.

Alternatively, or in addition thereto, the method may be applied to treat one or more liquid streams. The liquid streams may be aqueous or non-aqueous streams and may contain aqueous and/or organic components. Examples of liquid streams that may be processed include liquor from anaerobic digestion processes which contains organic compounds, such as those produced by an apparatus for the continuous digestion of organic matter is disclosed in U.S. Pat. No. 5,637,219. Other liquid streams that may be processed or treated include sewage, municipal and industrial wastewater liquid streams which contain nutrient feedstocks for the microorganisms, liquid streams containing carbon dioxide from water stripping of flue gases, solvent liquid streams such as perfluorocarbon solvents that contain dissolved $CO_2$.

Particular liquid medium compositions, nutrients, etc. required or suitable for use in maintaining a growing algae or other photosynthetic organism cultures are well known in the art. A wide variety of liquid media can be utilized in various forms for various embodiments of the present invention, as will be apparent to a person skilled in the art. Potentially appropriate liquid medium components and nutrients are, for example, discussed in detail in: Rogers, L. J. and Gallon J. R. "Biochemistry of the Algae and Cyanobacteria," Clarendon Press Oxford, 1988; Burlew, John S. "Algal Culture: From Laboratory to Pilot Plant." Carnegie Institution of Washington Publication 600. Washington, D.C., 1961; and Round, F. E. The Biology of the Algae. St Martin's Press, New York, 1965.

The fluid stream to be treated may also contain solid material, such as entrained or suspended solid particles. Typically, the solid materials will undergo little or no treatment by the microorganisms.

The method of the present invention employs the action of microorganisms to treat the fluid stream, in particular microorganisms that are phototrophic and function normally in the presence of light. Suitable microorganisms for use in the present invention are known in the art. The term 'microorganisms' as used herein is to be understood to include microorganisms and cultures of plant tissue that function in a like manner.

The microorganisms are retained in the liquid medium within the contacting zone, most preferably in the form of a suspension.

Suitable phototrophic microorganisms are known in the art. Examples of suitable microorganisms are disclosed by Morita, M., Y. Watanabe, and H. Saiki, "Instruction of Microalgal Biomass Production for Practically Higher Photosynthetic Performance Using a Photobioreactor." Trans IchemE. Vol. 79, Part C, September 2001. Suitable strains include all organisms capable of photosynthetic growth, such as plant cells, seaweed cells, and micro-organisms, including algae, photosynthetic bacteria and cyanobacteria in unicellular or multi-cellular form that are capable of growth in a liquid phase and may also include organisms modified artificially or by gene manipulation. The present invention may employ a single strain of microorganism. Alternatively, a plurality of different strains and classes of microorganism may be employed. Examples of species of algae include *Chlorella, Chlamdomonas, Chaetoceros, Dunaliella, Porphyridum, Haematococcus, Botryococcus, Euglena, Scenedesmus, Nitzschia, Stichococcus, Isochrysis, Cyclotella, Tetraselmis, Monoraphidium, Spirulina, Anabaena, Chlorogleopsis, Nostoc, Synechococcus, Phormidium, Aphanizomenon, Prorocentrum, Emiliania huxleyi*. The examples of classes of phototrophs include Cyanophyceae (blue-green algae), Chlorophyceae (green algae), Bacillariophyceae (including the diatoms), Chrysophyceae (including golden algae), Coscinodiscophyceae, Chlorarachniophyceae, Prasinophyceae, Raphidophyceae, Dictyochophyceae, Tribophyceae, Eustigmatophyceae, Cryptophyceae, Dinophyceae, Euglenophyceae, Prymnesiophyceae, Rhodophyceae, photosynthetic prokaryotes, photosynthetic archaebacteria and photosynthetic protoplast constructs.

The method involves the action of an impeller to enhance the contact between the fluid stream being treated and the microorganisms in the liquid phase. As described hereinbefore, the enhanced contact should be achieved while keeping the shear to which the microorganisms are subjected to a minimum. When the fluid stream to be treated is a liquid miscible with the microorganism-containing liquid phase, ensuring adequate contact between the microorganisms and the stream to be treated simply requires that the streams are brought together with gentle agitation from the impeller. More aggressive agitation may be required in the case that the stream to be treated is a liquid immiscible with the liquid phase containing the microorganisms.

The impeller should promote contact between the liquid phase containing the microorganisms and the fluid phase being treated, while preferably allowing the two phases to flow through the reactor vessel in a laminar flow regime.

A particular problem exists when the fluid stream to be treated is a gas. It is not possible to provide an intimate mixture between the gaseous and liquid phases without exposing the microorganisms to high levels of shear. Thus, the use of gas distributors, such as spargers and the like as known in the art, is to be avoided in the present invention. Rather, in such a case, the method is preferably conducted with the gaseous stream occupying a first region of the contacting zone and the microorganism-containing liquid phase occupying a second region of the contacting zone. The impeller is arranged to move from the second region of the contacting zone to the first region, taking with it liquid and microorganisms from the first region to the second region. Gas from the first region is drawn into the liquid medium in the second region as the impeller passes back into the second region and is subsequently released within the body of the liquid medium to return to the first region under the action of its buoyancy within the liquid medium.

The speed of rotation of the impeller is generally low, to reduce shear forces in the liquid phase and prevent excessive frothing of the liquid phase. The speed of rotation of the impeller is preferably in the range of from 0.5 to 80 rpm, more preferably from 1 to 60 rpm. The acceptable speed of rotation of the impeller will depend upon the physical properties of the liquid phase, as well as the shape and configuration of the impeller itself.

In the method of the present invention, the contacting zone may contain one or a plurality of fluid phases, depending upon the nature of the fluid stream being processed and its components.

In one embodiment, the contacting zone contains a single liquid phase, whereby the fluid stream being processed is a liquid stream that is miscible with the microorganism-containing liquid medium, most likely an aqueous system. Suitable liquid streams that can be processed in this embodiment are aqueous waste streams and streams containing organic liquids that are miscible with water, such as alcohols, aldehydes, ketones and the like.

In a further embodiment, the contacting zone contains two liquid phases, a first liquid phase is the microorganism-containing liquid medium, with the second liquid phase being a liquid stream being processed or a second liquid medium used, for example to remove components from the microorganism-containing liquid, that contains components that are not miscible with the microorganism-containing liquid medium. Examples of liquids that are not miscible with an aqueous microorganism-containing medium are non polar organic solvents, alkanes, such as dodecane and hexane, and perfluoro solvents, such as may be used to extract metabolites from the aqueous microorganisms-containing phase.

A further embodiment of the present invention is one in which the contacting zone contains three or more liquid phases. In addition to the microorganism-containing liquid medium, the contacting zone may have supplied thereto two liquid streams to be processed. Alternatively, one of the liquid phases may comprise the liquid stream to be processed and a second liquid phase may be fed to the contacting zone to carry out solvent extraction of components from one or more of the other liquid phases.

Still further, the method of the present invention may operate with a liquid phase containing the microorganisms, to process or treat a gaseous stream. The contacting zone may be provided with one or more additional, immiscible liquids, present as separate phases within the contacting zone, which may function as described above, for example to remove components from the contacting zone, such as by solvent extraction.

Examples of liquid components that may be supplied to the contacting zone to effect solvent extraction include perflurocarbons, details of which are provided below.

Solvent-containing liquid streams may be introduced into the contacting zone so as to flow co-currently with the microorganism-containing liquid medium or counter-currently.

In one embodiment of the present invention, a gaseous stream is being processed or treated, in particular a flue gas or the like. It is particularly advantageous that the gas stream being fed to the contacting zone is not intimately mixed with the microorganism-containing liquid phase, but rather is kept as a substantially separate or discrete phase. Contact between the microorganisms and the gaseous stream being processed is enhanced by the rotating impeller generating a high liquid surface area within the gaseous phase. In this way, gaseous products of the action of the microorganisms are removed by the gaseous stream. In particular, in many cases the by product of the action of the microorganisms on the fluid stream being processed is oxygen. High concentrations of oxygen in the microorganism-containing liquid medium will act as a poison and adversely affect the action of the microorganisms, eventually destroying the active microorganism population. The action of the substantially separate gaseous phase is to remove the oxygen from the microorganism-containing medium, thus maintaining the activity level of the microorganisms.

Further, it has been found that the action of the substantially separate gaseous stream and the rotating impeller reduces the formation of small diameter gas bubbles within the microorganism-containing liquid medium. Gas bubbles of small diameter pass through the liquid medium and in so doing generate a high shear on the surrounding liquid and microorganisms. The method and apparatus of the present invention prevent the formation of small bubbles, for example by appropriate design of the impeller and rotor assembly, and/or allow the small bubbles to rapidly coalesce, thus reducing the shear applied to the microorganisms.

In a further embodiment of the present invention, in the event that the fluid stream to be processed is liquid, it may be advantageous to feed a gaseous stream to the contacting zone, in order to allow gaseous products and metabolites of the action of the microorganisms, such as oxygen, to be removed, as hereinbefore described. In this way, gases building up in the contacting zone may be effectively scavenged and removed.

The gaseous stream, whether the fluid stream being processed or not, may be introduced into the contacting zone so as to flow co-currently with the one or more liquid phases or counter-currently.

As noted above, one or more solvents may be introduced into the contacting zone to remove components by solvent extraction. Suitable solvents for use in this manner are known in the art. Particularly preferred solvents for use in the present invention are perfluorocarbons. Perfluorinated compounds (PFCs) have low reactivity and high chemical stability due to the high energy of their C—F bonds. They have high boiling points and low vapour pressures because of the strength of the C—F bond and the high molecular weight. They also have no dipole and very low molecular interactions due to the repulsive tendency of fluorine atoms. These unique properties lead to high gas solubility, minimum vapor losses, and low forces required for expelling the gas molecules upon decreasing pressure or increasing temperature. Examples of suitable perfluorocarbons include: Perfluoro-perhydrofluorene ($C_{13}F_{22}$), Perfluoro-perhydrophenanthrene ($C_{14}F_{24}$), and Perfluoro-cyclohexylmethyldecalin ($C_{17}F_{30}$), known as PP10, PP11, and PP25

Gases are approximately twice as soluble in fluorocarbons than in the corresponding hydrocarbon, a fact attributed to their extremely low intermolecular cohesion, as is also seen in very low solubility parameters and surface tension values. The solubility is proportional to the gas partial pressure. In particular, perfluorocarbons are water immiscible liquids that dissolve 10 to 20 times more oxygen than does water. These fluids can be used for bubble-free oxygenation and removal of excess carbon dioxide in the method of the present invention. Further, perflurocarbons may be used in stripping oxygen produced by the microorganisms, to prevent the build up of high oxygen concentrations, in turn reducing the inhibitory effects of oxygen on the microorganism activity.

Examples of suitable perfluorocarbons for use as solvents in the present invention include perfluorodecalin ($C_{10}F_{18}$), a bicyclic perfluorinated alkane, and bromoperfluoro-n-octane (perfluorooctyl bromide (PFOB); empirical formula: $C_8F_{17}Br$). Other examples include perfluoro hexane, perfluoro methylcyclohexane, pefluoro-1,3-dimethylcyclohexane and perfluoro methyl decalin.

As noted above, the contacting zone may comprise solid material. This may enter the contacting zone entrained or suspended in one or more of the fluid streams. Movement of the solid material through the contacting zone to prevent its build-up is preferred, as described above.

Solid material may also be supplied to the contacting zone, in particular solid particles that may act as a substrate for the microorganisms. In one preferred embodiment, the solid substrate for the microorganisms has a density less than that of the microorganism-containing liquid medium, allowing the solid substrate to float. The impeller is preferably designed to move the solid substrate from the microorganism-containing medium into the fluid stream being processed, as described above.

In a further embodiment, solid material may be introduced into the contacting zone to absorb or adsorb one or more components from one or more fluid phases within the contacting zone. The solid material may have a density that is less than, the same as or greater than the density of the liquids in the contacting zone.

Examples of solid absorbents and adsorbents include affinity sorbants, antibody sorbants and solid phase sorbants, such as activated carbon, ion-exchange resins, and the like.

Solid material, if introduced, may be introduced into the contacting zone so as to flow co-currently with the liquid phases in the contacting zone or countercurrently.

The method of the present invention may be operated with the contacting zone at any suitable pressure. In many cases, in particular when the method is used to process flue gas or the like, the pressure within the contacting zone may be superatmospheric, in particular from 0.01 to 2 bar, more preferably from 0.01 to 1 bar above atmospheric pressure. However, higher pressure may be employed if required to meet the processing requirements. Similarly, the contacting zone may be operated at pressures below atmospheric pressure, if desired.

Similarly, the contacting zone may be operated at any suitable temperature that is appropriate to sustain and optimise the function and growth of the microorganisms. Suitable operating temperatures will depend upon the particular microorganisms being employed and will be readily determinable by a person skilled in the art.

The method of the present invention relies upon at least a portion of the vessel in which the contacting zone is housed being transparent to the passage of light, in order to provide the microorganisms with the requisite amount or intensity of light for stable activity and growth. In order to ensure that sufficient light is provided to the microorganisms, it is preferred that the method includes cleaning the interior surface of the vessel either continually or intermittently, as required. Suitable means for cleaning the inner surface of the vessel are as hereinbefore described. As noted above, a particularly preferred method includes providing a wiper assembly to contact the relevant surfaces and to move the wiper assembly in a reciprocating motion.

In addition, low density or floating solid materials may be introduced into the contacting zone in order to clean the inner surface of the vessel in which the contacting zone is housed. Suitable floating cleaning means include plastic balls, beads or the like, which abrade the surface of the vessel to remove accumulated deposits and microorganisms.

The method of the present invention provides a number of products. First, the method provides a treated fluid stream. Thus, in the case of a flue gas, the method is particularly suitable at removing carbon dioxide from the flue gas stream before it is exhausted to the atmosphere. The method of the present invention is particularly suitable for this, as it does not require the flue gas to be compressed before being treated and the flue gas can be introduced into the contacting zone at its normal operating pressure, typically 0.01 to 2 bar above atmospheric pressure, more preferably from 0.01 to 1 bar above atmospheric pressure.

In addition, the method produces microorganisms, which must be removed from the contacting zone either continuously or intermittently, for example by the continuous or intermittent removal of the microorganism-containing liquid medium. To ensure the maintenance of the proper and healthy population of microorganisms, it is preferred that the microorganism-containing liquid medium is supplemented with fresh liquid medium and fresh microorganisms on a continuous or periodic basis. The microorganisms removed from the contacting zone may be harvested using conventional techniques known in the art. Techniques for harvesting the thus produced biomass include centrifugation, tangential flow filtration, sedimentation, and dissolved air floatation.

The thus harvested microorganisms may have a variety of further uses. Examples include inclusion in fertilisers and animal feeds. In one preferred embodiment, the harvested biomass is used in the manufacture of biofuel. Suitable techniques for the conversion of harvested microorganisms into biofuel are known in the art. A variety of methods for conversion of the biomass materials into biodiesel are known in the art. For example, the algae may be harvested, separated from the liquid medium, lysed and the oil content separated. The algal-produced oil will be rich in triglycerides. Such oils may be converted into biodiesel using well-known methods, such as the Connemann process, as described U.S. Pat. No. 5,354,878. Transesterification processes are known and involve an alkaline catalyzed transesterification reaction between the triglyceride and an alcohol, typically methanol. The fatty acids of the triglyceride are converted to methanol, producing alkyl esters (biodiesel) and releasing glycerol. The glycerol can be removed and may be used for other purposes.

The dried algae biomass recovered from drying can be utilized directly as a solid fuel for use in a combustion device and/or could be converted into a fuel grade oil, such as biodiesel and/or a combustible organic fuel gas. In certain embodiments, at least a portion of the biomass, either dried or before drying, can be utilized for the production of products comprising organic molecules, such as fuel-grade oil and/or organic polymers. Algal biomass intended for use in fuel-grade oil production, fuel gas production or the like can be decomposed in a pyrolysis or other known gasification processes and/or a thermochemical liquefaction process to produce oil and/or combustible gas. Such methods of producing fuel grade oils and gases from algal biomass are well known in the art, for example Dote, Yutaka, "Recovery of liquid fuel from hydrocarbon rich microalgae by thermochemical liquefaction," Fuel. 73: Number 12. (1994); Ben-Zion Ginzburg, "Liquid Fuel (Oil) From Halophilic Algae: A renewable Source of Non-Polluting Energy, Renewable Energy," Vol. 3, No 2/3. pp. 249-252, (1993); Benemann, John R. and Oswald, William J., "Final report to the DOE: System and Economic Analysis of Microalgae Ponds for Conversion of $CO_2$ to Biomass." DOE/PC/93204-T5, March 1996; and Sheehan et al., 1998.

Further, the method may be used to produce high value primary and secondary metabolites from the microorganisms, which have significant further and end uses. In this respect, reference is made to Singh, Sawraj; Kate, Bhushan N; Banerjee, U C; 'Bioactive Compounds From Cyanobacteria and Microalgae: An Overview'; Critical Reviews in Biotechnology 2005; Pauline Spolaore, Claire Joannis-Cassan, Elie Duran, and Arsène Isambert. 'Commercial Applications of Microalgae'; Journal of Bioscience and Bioengineering; Vol. 101, No. 2, 87-96. 2006; and 'Micro- and Macro-Algae: Utility for Industrial Applications'; Outputs from the EPOBIO project September 2007; prepared by Anders S Carlsson, Jan B van Beilen, Ralf Möller and David Clayton (EPOBIO: Realising the Economic Potential of Sustainable Resources—Bioproducts from Non-food Crops) September 2007, CNAP, University of York. ISBN 13: 978-1-872691-29-9.

The method may provide one or more components, such as the aforementioned metabolites, which are recovered from the contacting zone, for example by means of solvent extraction within the contacting zone. The components may be removed from their respective solvent streams by techniques known in the art and applicable to the solvent in question.

To facilitate or improve separation of components within the contacting zone of the reactor assembly, a potential difference may be applied across the whole or a portion of the contacting zone, in order to have charged or polar molecules within the contacting zone migrate. One or more suitable outlets may be provided in the contacting zone to remove the charged or polar molecules collected in this manner. The potential difference may be applied in any suitable manner. In one embodiment, the potential difference is applied across the impellers of the rotor assembly. In particular, when using impellers in the form of elongate scoops or buckets, especially trough impellers, the potential difference may be applied along the length of the impeller, such that charged and/or polar molecules migrate within or along the impeller.

One important metabolite produced by some cyanobacteria and photosynthetic prokaryotes is hydrogen. Hydrogen finds use, for example as a source of bioenergy. Typically, photosynthetic bacteria, when grown anaerobically, consume organic acids, such as acetic acid and carbon dioxide, and produce hydrogen as a metabolite. In one embodiment, the present invention is operated to provide a source of organic acids to be consumed under anaerobic conditions, in order to produce hydrogen. The hydrogen is removed from the contacting zone and recovered for further use, in particular as a fuel.

BRIEF DESCRIPTION OF THE DRAWINGS

Embodiments of the present invention will now be described by way of example only, having reference to the accompanying drawings in which:

FIG. 11 is a longitudinal cross-sectional representation of a reactor assembly according to an alternative embodiment to that of FIG. 6;

FIG. 12a is a cross-sectional view of a first reactor pond embodiment of the present invention;

FIG. 12b is a cross-sectional view of a second reactor pond embodiment of the present invention;

FIG. 12c is a cross-sectional view of a third reactor pond embodiment of the present invention.

DETAILED DESCRIPTION OF THE INVENTION

Figure 1:
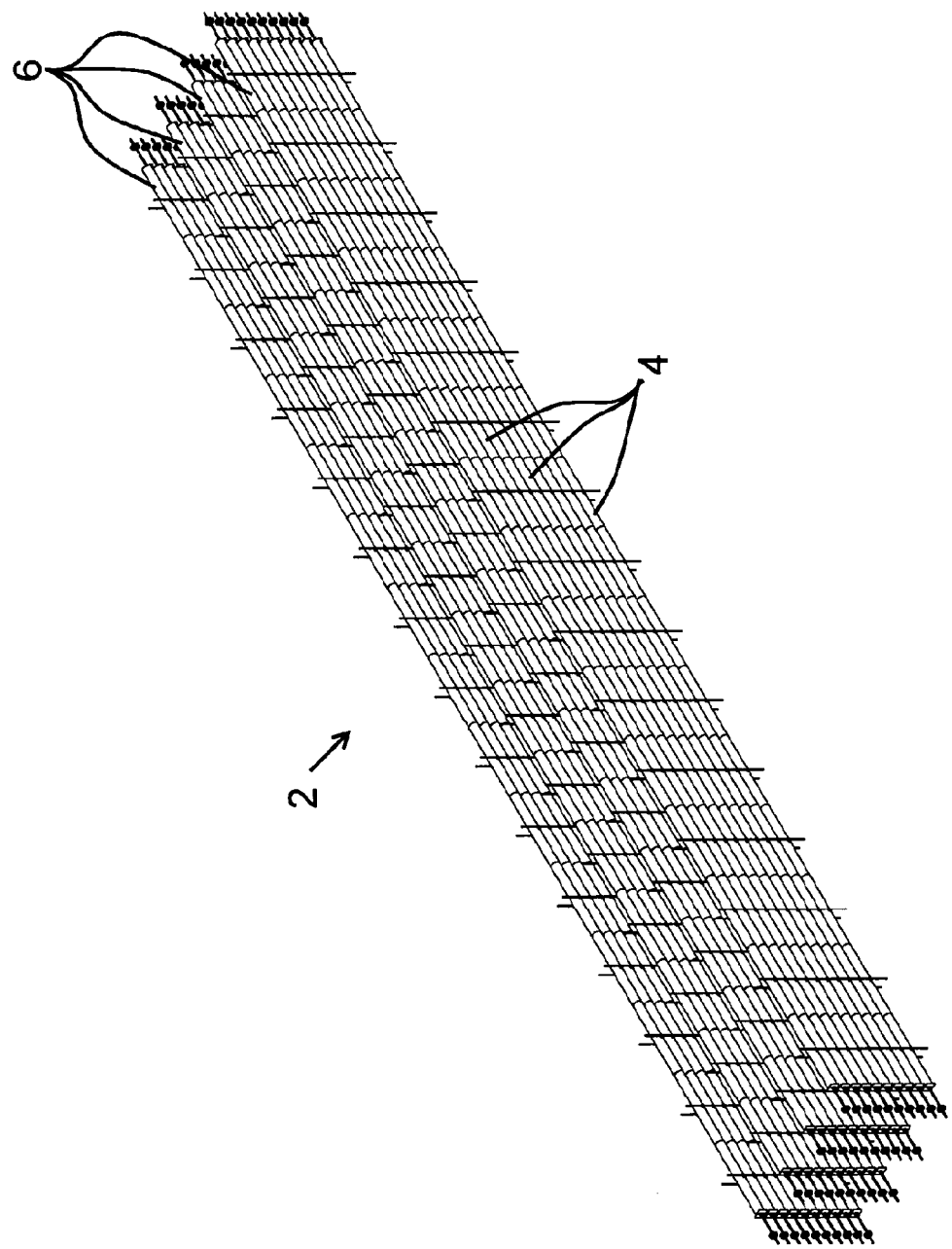
FIG. 1 is a perspective view of a bioreactor array comprising a plurality of bioreactors according to one embodiment of the present invention.

Referring to FIG. 1, there is shown a perspective view from one end of a bioreactor array according to one embodiment of the present invention and generally indicated as 2. The array 2 comprises a plurality of individual reactor assemblies 4, each of which is generally elongate and cylindrical in form, as described in more detail hereinafter. The reactor assemblies 4 are arranged in a plurality of stacks 6, the reactor assemblies in each stack being arranged vertically one above the other. The array 2 is positioned at a location and at an orientation so as to allow natural light to irradiate the walls of the reactor assemblies. In particular, the array 2 is preferably arranged such that sunlight is incident on the cylindrical side walls of the reactor assemblies 4 throughout as much of the day as possible. The optimum position an orientation for an array will be readily determinable by the person skilled in the art at each intended location.

Figure 2:
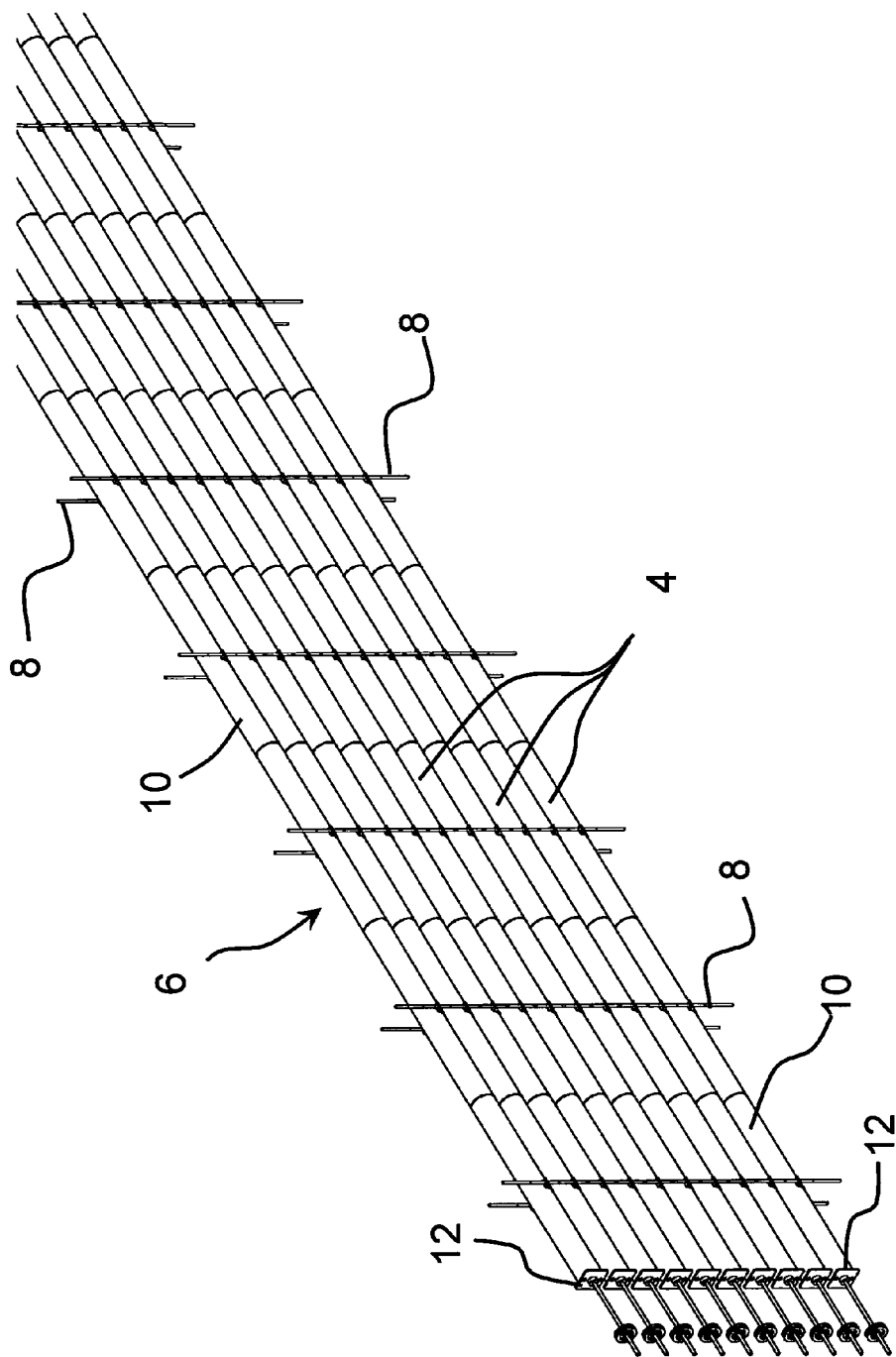
FIG. 2 is a perspective view of a portion of the array of FIG. 1.

A single stack 6 of reactor assemblies 4 is shown in perspective view in FIG. 2. As can be seen, in the stack shown, ten reactor assemblies 4 are retained in a vertical arrangement by means of supporting frames 8 disposed at intervals along the length of the reactor assemblies.

It is to be understood that the array shown in FIG. 1 and the stack shown in FIG. 2 is just one of many possible arrangements for the reactor assemblies 4 of the present invention. It is a feature of the reactor assembly that it may be formed in any suitable size and arranged in any suitable configuration that makes the optimum use of the location and the available natural and sun light. The reactor assemblies may be arranged singly or in an array, such as shown in FIGS. 1 and 2. The assembly or array may be disposed at ground level or may be in an elevated position above the ground, for example being disposed on the roof of a building. In this way, the reactor assemblies may be disposed very close the source of the fluid stream to be treated. For example, one or more reactor assemblies may be disposed adjacent the flue gas outlet of a boiler for treating the flue gas and removing carbon dioxide therefrom.

Figure 3:
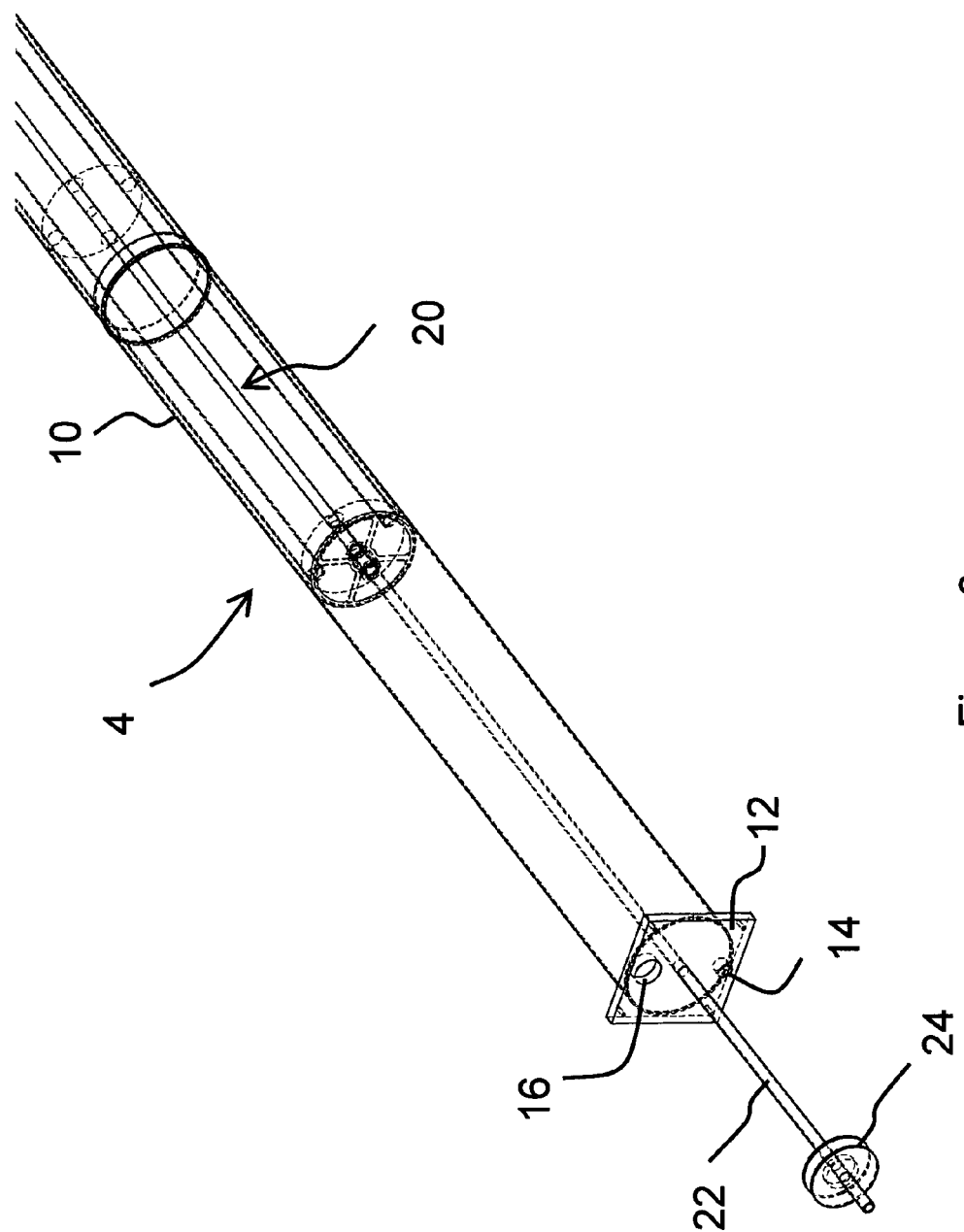
FIG. 3 is a perspective view of one end of a single reactor assembly of the array of FIG. 1.

A single reactor assembly 4 is shown in more detail in FIG. 3. Each reactor assembly 4 comprises a generally cylindrical, elongate reactor vessel 10 having an end plate 12. The reactor vessel 10 is formed from a transparent material, at least along part of its length, most preferably along its entire length. Suitable transparent materials are known in the art and include polyethylene, polypropylene, polyurethane, polycarbonate, polyvinylpyrrolidone, polyvinylchloride, polystyrene, poly(ethylene terephthalate), poly(ethylene naphthalate), poly(1,4-cyclohexane dimethylene terephthalate), polyolefin, polybutylene, polyacrylate and polyvinlyidene chloride, per-fluoro plastics, PTFE, PET, soda glass, borosilicate glass, and quartz glass. The reactor vessel is preferably rigid. However, in an alternative arrangement (not shown for clarity), the reactor vessel is flexible and retained in a generally cylindrical form by rigid support members. The end plate 12 may be of the same or similar material as the reactor vessel 10. Alternatively, the end plate may be formed from an opaque material, for example a metal such as stainless steel or the like.

The end plate 12 is provided with a first opening 14 in its lower portion, forming an inlet for supplying a liquid microorganism-containing medium to the reactor vessel. A second opening 16 is provided in the upper portion of the end plate 12 to form an inlet for a fluid stream to be treated. In the embodiment shown in FIG. 3, the second opening 16 is sized to allow a gaseous stream to be fed into the reactor vessel for treatment by the microorganisms therein. An end plate (not shown for clarity) is provided at the opposite end of the reactor vessel and has corresponding openings to openings 14 and 16, to provide outlets for the liquid microorganism-containing liquid and the treated gaseous stream. The end plates may be provided with additional openings in an analogous manner, as required, to allow further fluid streams to be fed to the reactor vessel, as required for the proper operation of the reactor assembly.

The openings in the end plates are connected to suitable supply lines and headers for supplying and removing fluid streams to and from the reactor vessel (omitted for clarity).

The reactor assembly 4 is provided with a rotor assembly 20 extending longitudinally within the reactor vessel 10. The rotor assembly 20 is mounted on a shaft 22 extending longitudinally within the reactor vessel and outwards therefrom through the end plate 12. The shaft 22 is provided with a sprocket 24 at its end, allowing the shaft to be rotated by a suitable motor or other drive mechanism (again omitted from the figures for clarity). Any suitable drive system for rotating the shaft of the rotor assembly 20 may be employed.

Figure 4:
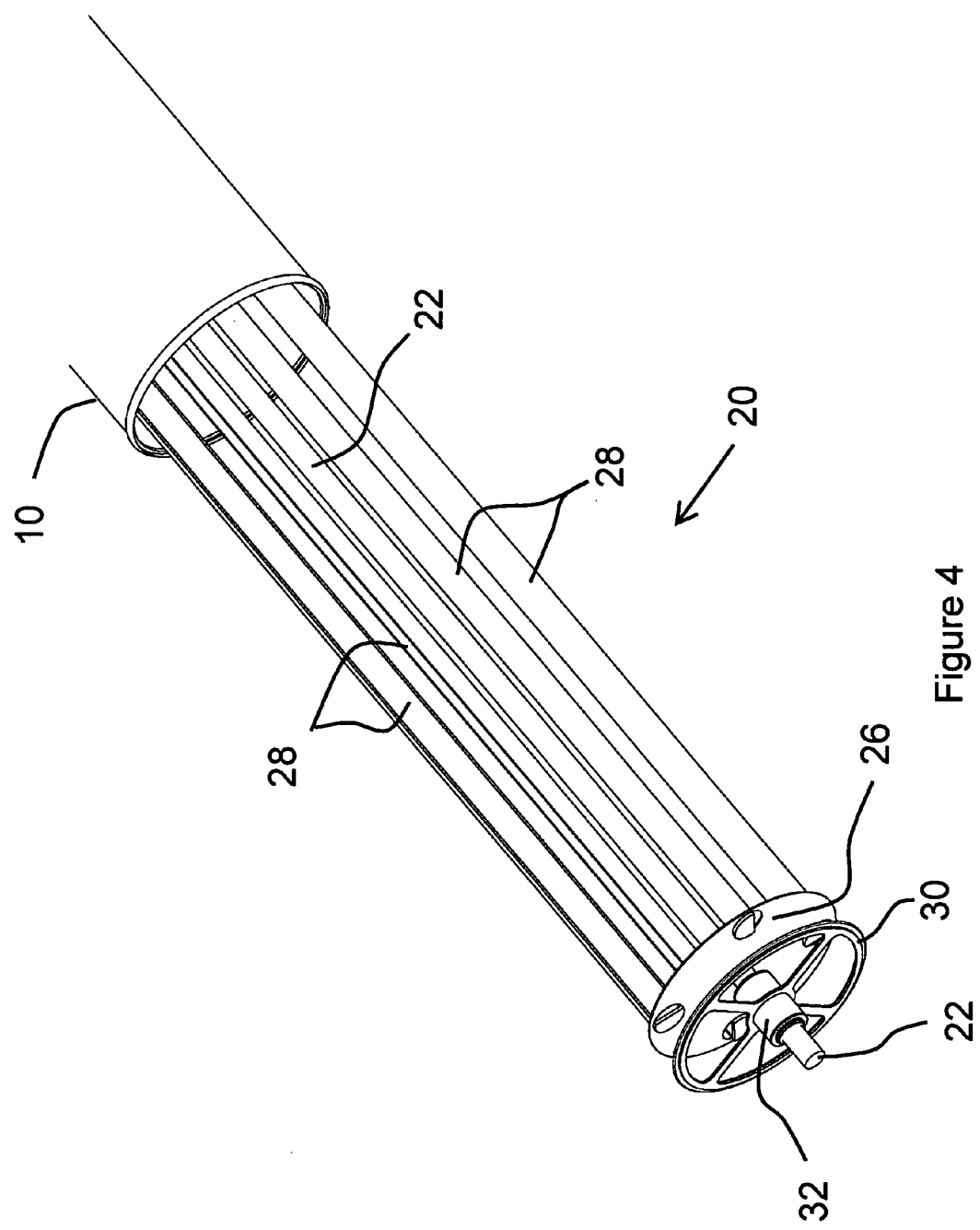
FIG. 4 is a perspective view of a rotor assembly of the reactor assembly of FIG. 3 partially withdrawn from the reactor vessel.

The rotor assembly 20 is shown in more detail in FIG. 4, which shows the rotor assembly partially withdrawn from the reactor vessel 10. The rotor assembly 20 comprises a circular rotor plate 26 mounted to the shaft 22, so as to be rotatable therewith. A plurality of elongate troughs 28 extend from the rotor plate 26. The troughs 28 are mounted at their ends in respective openings in the rotor plate 26 and are spaced equally around the circumference of the rotor plate. A second rotor plate (not shown in FIG. 3 and within the reactor vessel 10) supports the opposing end of each trough 28.

The rotor assembly may be provided with a plurality of pairs of rotor plates 26, each with respective troughs extending therebetween, which serve to divide the interior of the reactor vessel 10 into discrete portions or compartments. In such a case, the rotor plates may be provided with suitable openings to allow for the passage of fluids between the adjacent compartments so-formed.

Figure 5:
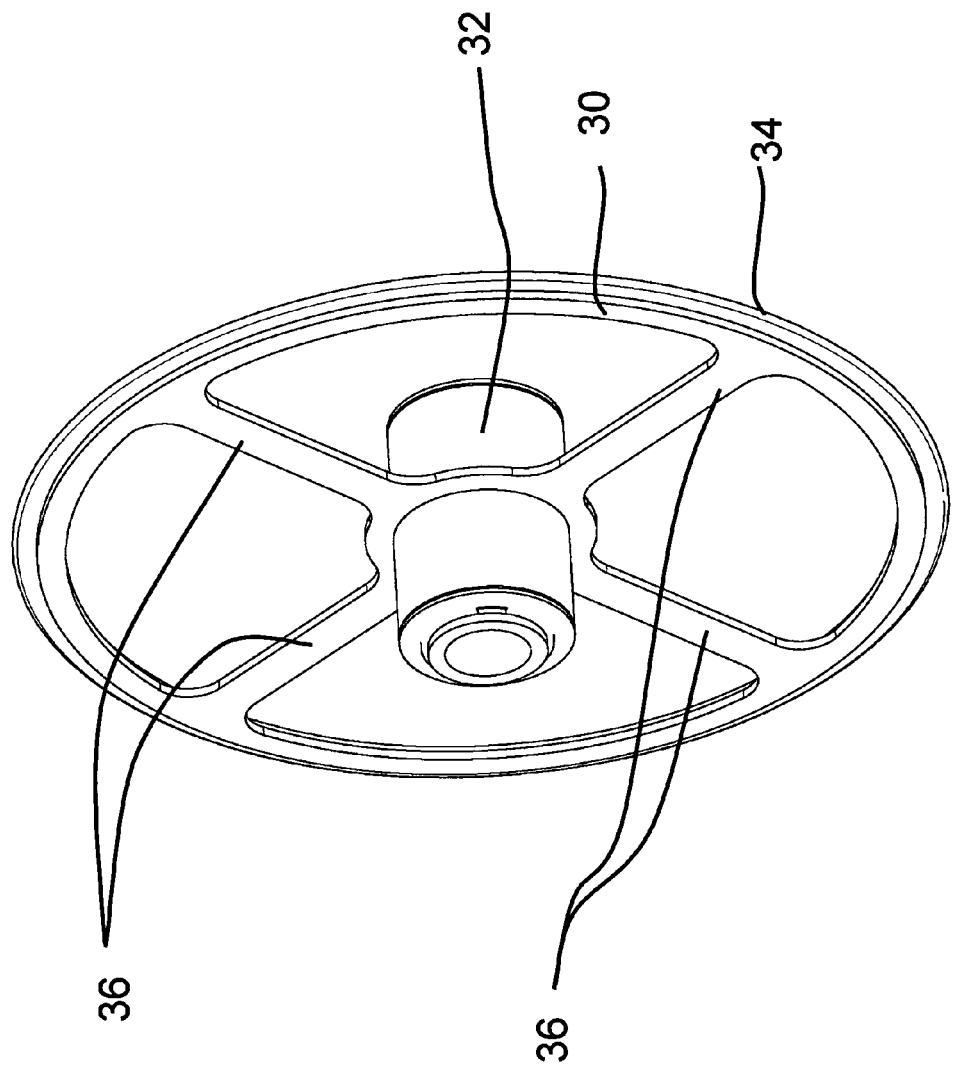
FIG. 5 is a view of a wiper ring of the rotor assembly of FIG. 4.

The rotor assembly 20 further comprises a wiper ring 30 mounted on a hub 32 housing a bearing assembly for the rotor assembly 20 and the shaft 22. The wiper ring 30 is provided at its circumference with a flexible wiper blade 34. Details of the wiper ring 30 are shown in FIG. 5, where the ring 30 is connected by spokes 36 to the hub 32. Fluid within the reactor vessel may move freely past the wiper ring through the openings between the spokes 36 as the wiper ring is moved.

When the rotor assembly 20 is in position in the reactor vessel 10, the wiper blade 34 bears upon the inner surface of the reactor vessel. The rotor assembly 20 and its drive mechanism are arranged to reciprocate longitudinally within the reactor vessel 10 when in operation, causing the wiper blade 34 to pass over the inner surface of the reactor vessel and remove accumulated deposits and growths of microorganisms. This in turn ensures that light is able to pass through the transparent wall of the reactor vessel and into the liquid microorganism-containing medium.

Figure 6:
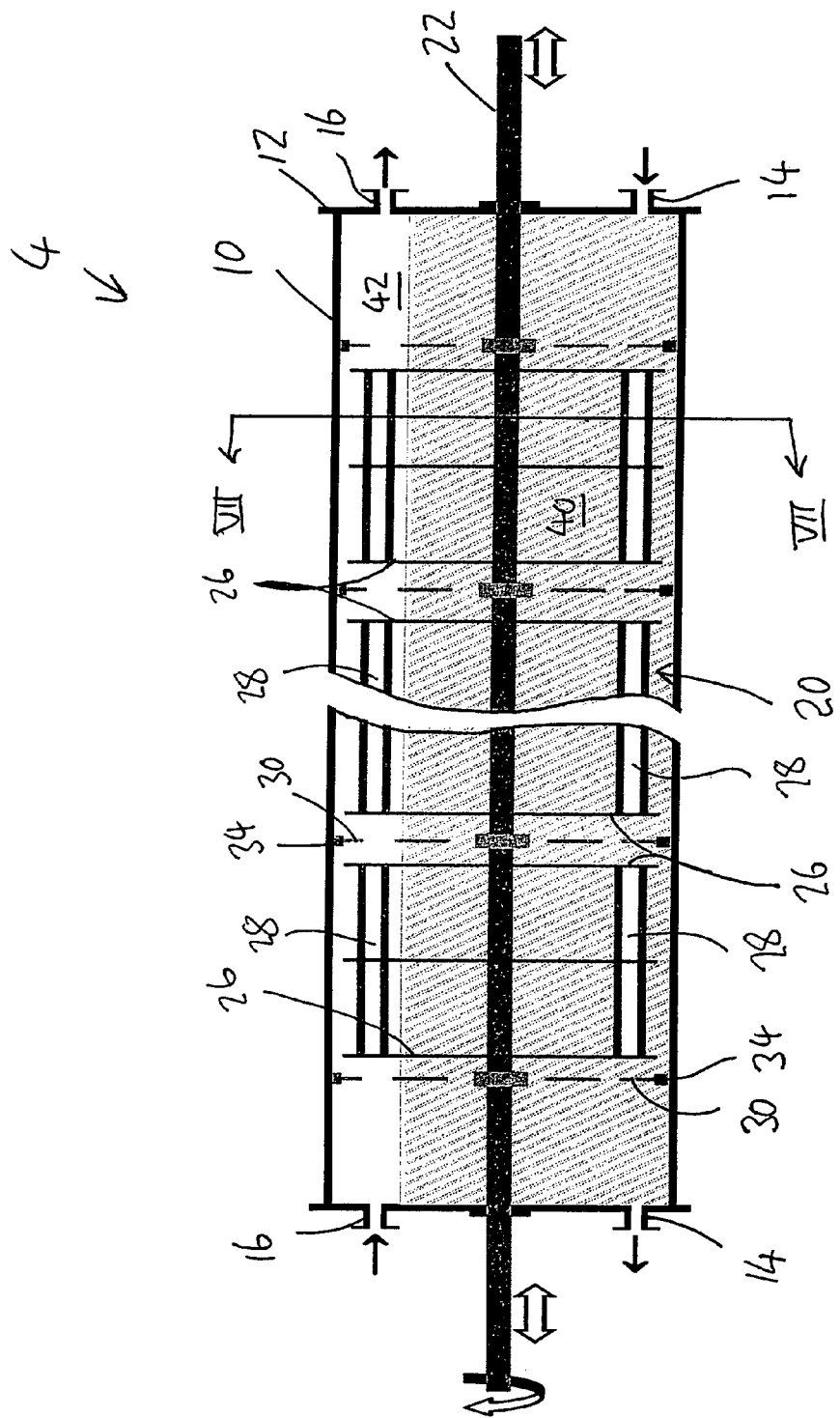
FIG. 6 is a longitudinal cross-sectional representation of a reactor assembly according to one embodiment of the present invention.
Figure 7:
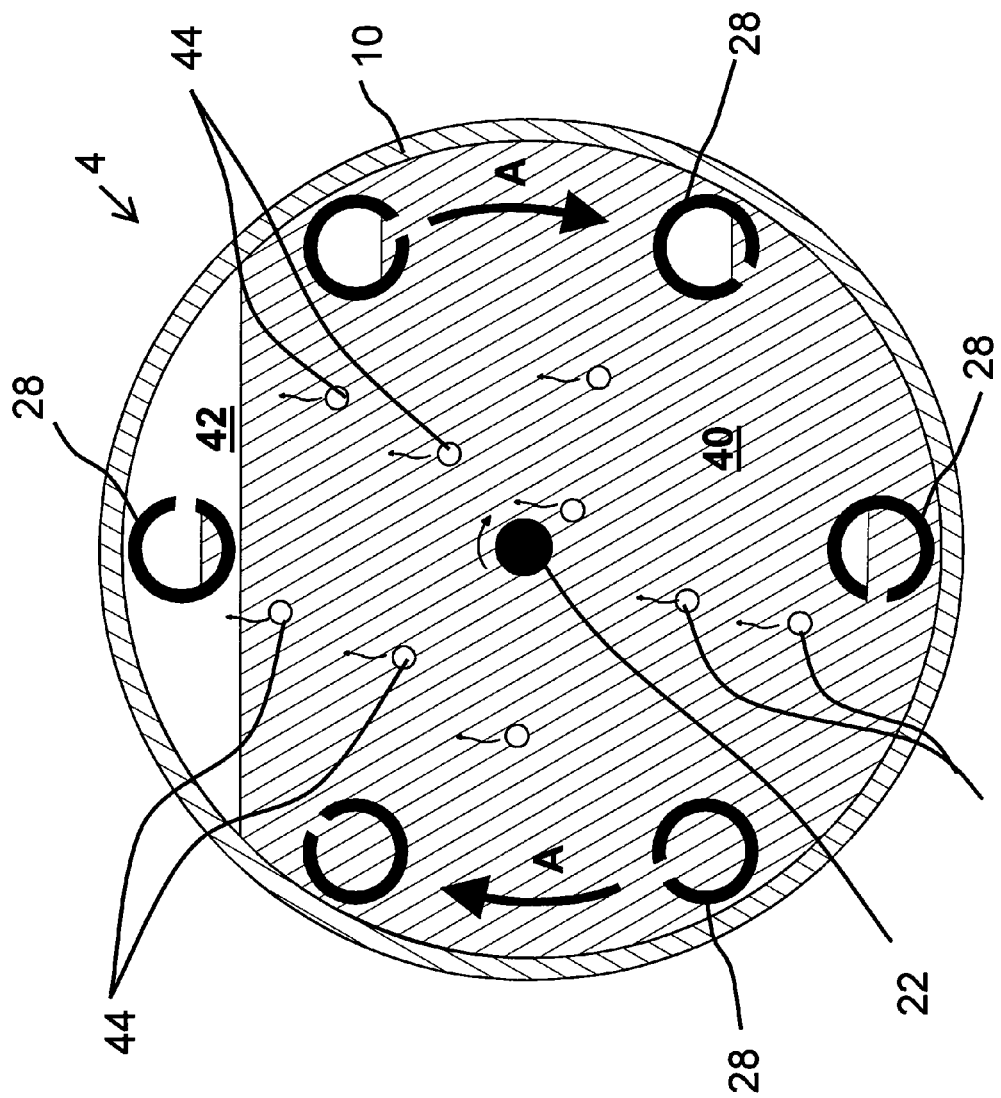
FIG. 7 is a transverse cross-sectional representation of the reactor assembly of FIG. 6 along the line VII-VII.

A longitudinal cross-sectional representation of the reactor assembly 10 in operation is shown in FIG. 6, with a transverse cross-sectional view of the same being shown in FIG. 7. In the reactor assembly 4 shown in FIG. 6, the reactor vessel 10 is provided with an end plate 12 at each end, each end plate having respective openings 14 for supply and removal of liquid medium containing microorganisms and openings 16 for supply and removal of a fluid stream to be treated, for example a gaseous stream such as flue gas. In operation, an aqueous medium containing microorganisms is fed into the reactor vessel by way of an opening 14 in the appropriate end plate (as indicated by the arrows in FIG. 6), to provide a body of liquid microorganism medium 40 in a first region of the reactor vessel 10. A fluid stream to be treated, in particular a gas stream, such as flue gas containing carbon dioxide, is introduced into the reactor vessel through an opening 16 in the appropriate end plate (as indicated by the arrows in FIG. 6), to provide a body of a fluid to be treated in a second region 42 of the reactor vessel 10. The fluid stream to be treated has a lower density than that of the liquid microorganism-containing stream and, therefore, occupies a region above the liquid, as shown in FIGS. 6 and 7. It will be appreciated that the relative positions of the two fluid streams is reversed in the case that the fluid stream to be treated is more dense than the microorganism-containing liquid.

In operation, the rotor assembly 20 is rotated within the reactor vessel, causing the troughs 28 to follow the path indicated by arrows A in FIG. 7. Each trough passes from the first region of the reactor vessel, containing the body of microorganism-containing liquid, and into the second region containing the fluid to be treated. As shown in FIG. 7, the trough carries liquid from the first region 40 into the second region 42, increasing the contact between the two fluids. Further, fluid, for example gas as shown in FIG. 7, is carried from the second region 42 into the first region 40, again increasing the contact between the two fluid phases. The gas leaves the troughs 28 and forms large bubbles 44 which travel upwards within the liquid microorganism-containing medium and return to the region 42. The trough is formed such that the large bubbles are formed. Large bubbles generate significantly less shear when passing through a body of liquid than smaller bubbles and thus apply less shear to the microorganisms within the liquid medium.

As the bubbles of the fluid to be treated pass through the liquid medium, components, such as carbon dioxide, are consumed by the microorganisms in the liquid medium. The products of the metabolism of the microorganisms, such as oxygen are released into the bubbles, which then return to the bulk of the fluid stream in region 42 of the reactor vessel. The products of the metabolism of the microorganisms leave the reactor vessel in the fluid stream being treated, from where they may be removed as desired using known technology.

During the operation, the bulk flow of the liquid microorganism-containing medium and the fluid being treated is generally laminar through the reactor vessel, with the contact between the two phases being promoted in the manner described above. In this way, the microorganisms are subject to minimal shear forces and energy.

The liquid medium containing the microorganisms and the fluid stream to be treated may be caused to flow in a co-current flow pattern or a counter-current flow pattern through the reactor vessel, as may be required.

The arrangement and mode of operation shown in FIGS. 6 and 7 is suitable for the treatment of a wide range of fluid streams, in particular for the treatment of gaseous streams, especially gaseous streams containing carbon dioxide, such as flue gas streams.

Figure 8:
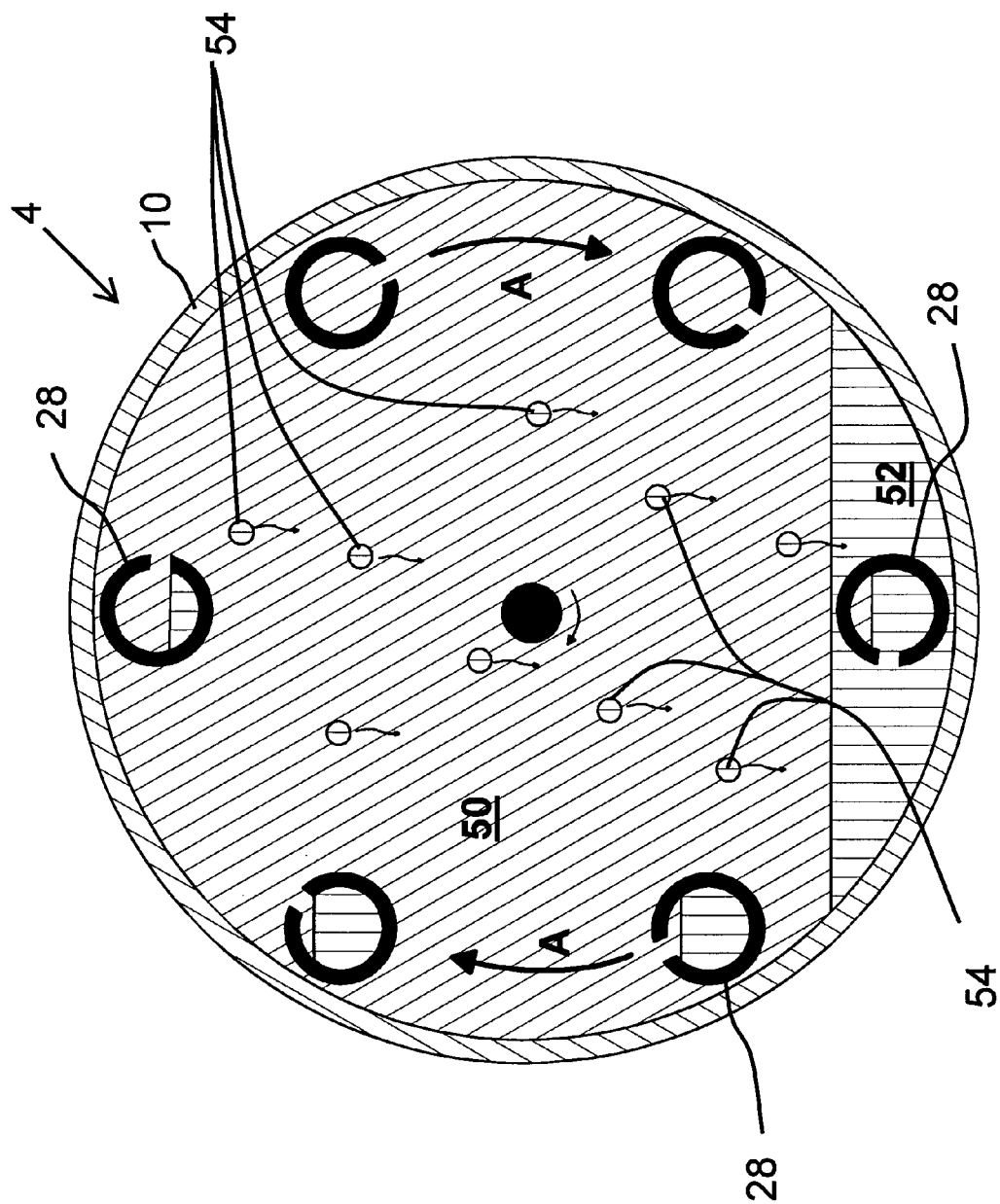
FIG. 8 is a transverse cross-sectional representation corresponding to that of FIG. 7 showing an alternative mode of operation of the reactor assembly.

An alternative mode of operation is shown in FIG. 8, which is a transverse cross-sectional view corresponding to that of FIG. 7 of the reactor assembly of FIG. 6, but operating under different principles as follows. An aqueous liquid medium containing microorganisms is fed into the reactor vessel as described hereinbefore and occupies a first region 50 of the reactor vessel. A gas exchange solvent, such as a perfluorinated hydrocarbon, is introduced into the reactor vessel and occupies a second region 52 of the reactor vessel. As the density of the gas exchange solvent is greater than that of the aqueous microorganism-containing medium, the gas exchange solvent occupies a region below the aqueous medium. Before being fed into the reactor vessel, the gas exchange solvent is contacted with a fluid stream to be processed, so as to remove one or more gaseous components therefrom, in particular to remove carbon dioxide from a gaseous stream, such as a flue gas or the like. Suitable apparatus and systems for contacting a gas exchange solvent with a gas stream are known in the art. The stream of gas exchange solvent containing the gas dissolved therein is then fed into the reactor vessel.

Contact between the microorganisms in the liquid medium and the gas exchange solvent is promoted in a manner analogous to the operation described above, with the bubbles 54 of gas exchange solvent captured by the troughs passing downwards through the microorganism-containing medium, as shown in FIG. 8. Gases, such as carbon dioxide, are consumed from the gas exchange solvent by the microorganisms. In addition, gaseous products of the microorganism metabolism, such as oxygen, are absorbed by the gas exchange solvent and leave the reactor vessel in the gas exchange solvent stream for subsequent recovery, as required. The gas exchange solvent may then be recycled to further contact the fluid stream to be processed.

Again, the flow of the liquid microorganism-containing medium and the gas exchange solvent may be either co-current or counter-current through the reactor vessel.

Figure 9:
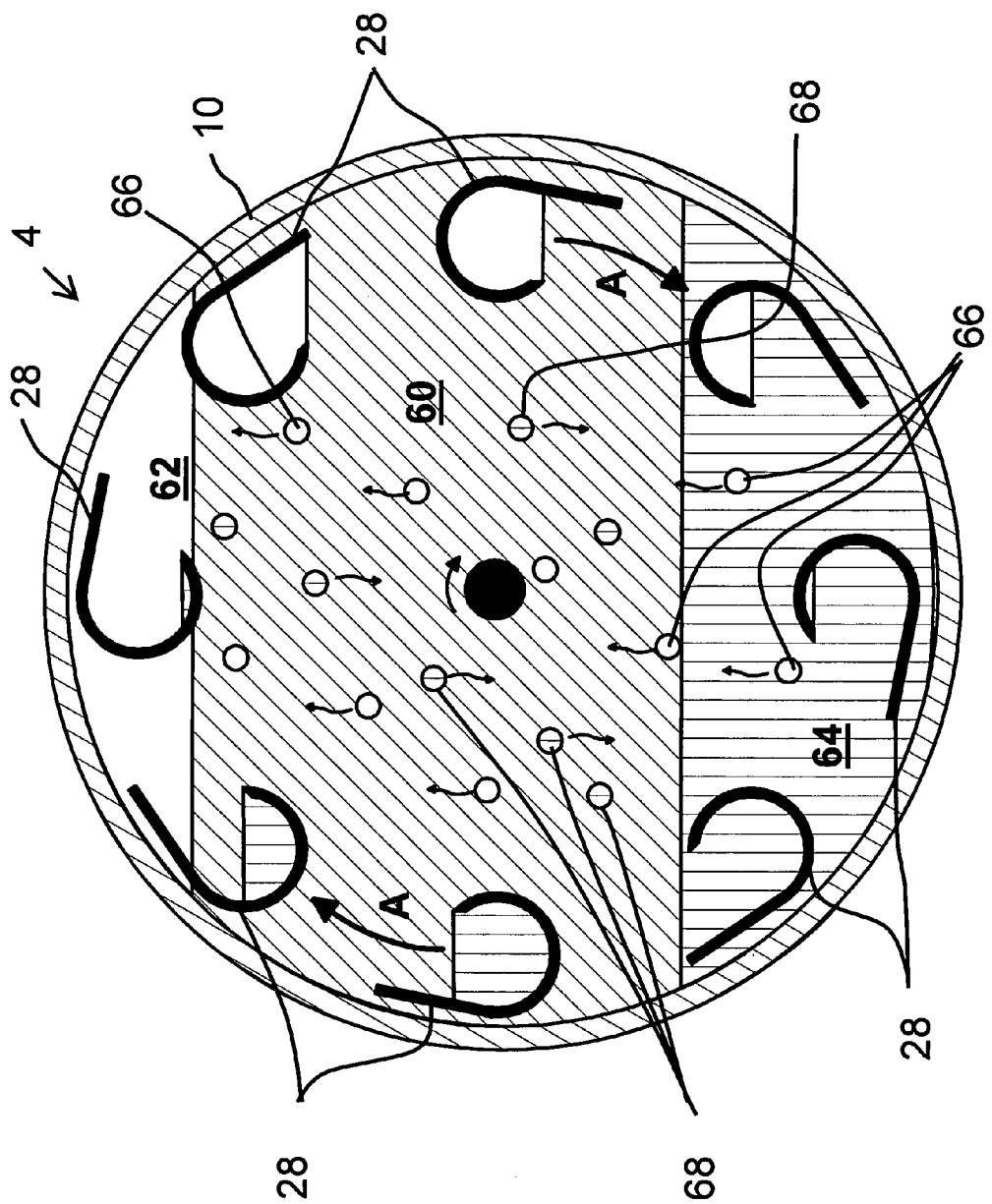
FIG. 9 is a transverse cross-sectional representation corresponding to that of FIG. 7 showing a further alternative mode of operation of the reactor assembly.

A further alternative mode of operation of the reactor assembly shown in FIG. 6 is represented in FIG. 9, which is a cross-sectional view corresponding that that of FIG. 7 but operating in the following manner. An aqueous liquid medium containing microorganisms is fed into the reactor vessel as described hereinbefore and occupies a first region 60 of the reactor vessel. A gaseous stream to be treated, for example a flue gas, is fed into the reactor vessel as described above and occupies a second region 62 of the reactor vessel, above the first region 60. A gas exchange solvent, such as a perfluorinated hydrocarbon, is introduced into the reactor vessel and occupies a third region 64 of the reactor vessel. As the density of the gas exchange solvent is greater than that of the aqueous microorganism-containing medium, the gas exchange solvent occupies a region below the aqueous medium. Before being fed into the reactor vessel, the gas exchange solvent may be contacted with a fluid stream to be processed, so as to remove one or more gaseous components therefrom, in particular to remove carbon dioxide from a gaseous stream, such as a flue gas or the like. Suitable apparatus and systems for contacting a gas exchange solvent with a gas stream are known in the art. The stream of gas exchange solvent containing the gas dissolved therein is then fed into the reactor vessel.

Contact between the microorganisms in the liquid medium, gases in the gas stream and the gas exchange solvent is promoted in a manner analogous to the operation described above, with the bubbles 66 of the gas captured by the troughs passing upwards through the microorganism-containing liquid medium and the bubbles 68 of the gas exchange solvent captured by the troughs passing downwards through the microorganism-containing medium, as shown in FIG. 9. Gases, such as carbon dioxide, are consumed from the gas stream and the gas exchange solvent, if present, by the microorganisms. In addition, gaseous products of the microorganism metabolism, such as oxygen, are absorbed by the gas exchange solvent and leave the reactor vessel in the gas exchange solvent stream or pass into the gas stream, for subsequent recovery, as required. Finally, gaseous components entering the reactor vessel in the gaseous stream but not consumed by the microorganisms may be recovered and removed by the action of the gas exchange solvent. This mode of operation is particularly advantageous as it allows carbon capture from streams such as flue gases and the like to continue during times of darkness or low light levels, when the conditions are not suitable for photosynthesis by the microorganisms. At such times, the capture of carbon in the form of carbon-containing gases is effected solely by the removal of such gases from the gaseous stream by the gas exchange solvent.

Again, the flow of the liquid microorganism-containing medium, the gas stream and the gas exchange solvent may be either co-current or counter-current through the reactor vessel, as required for optimum operation.

Figure 10:
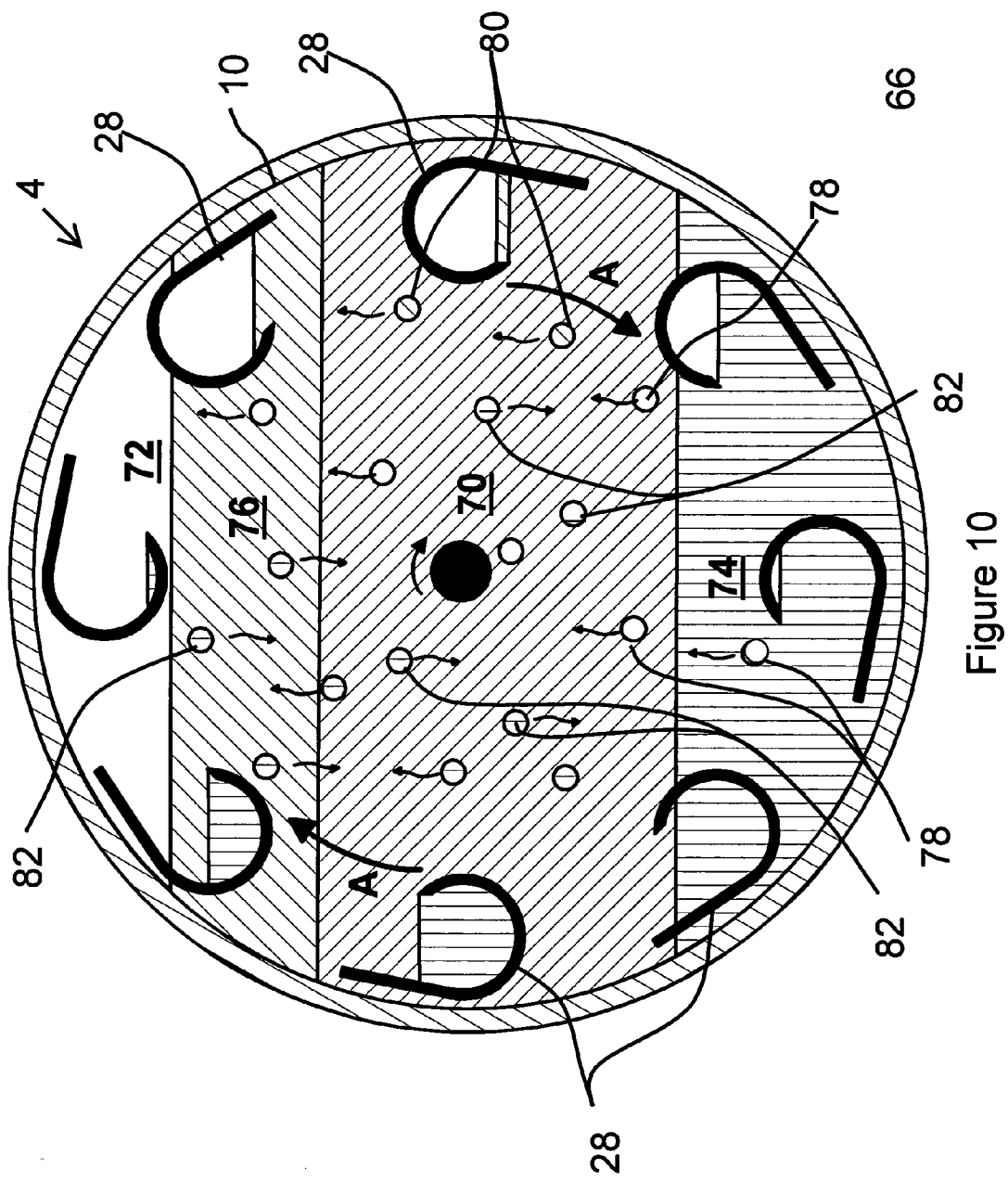
FIG. 10 is a transverse cross-sectional representation corresponding to that of FIG. 7 showing a still further alternative mode of operation of the reactor assembly.
Figure 17:
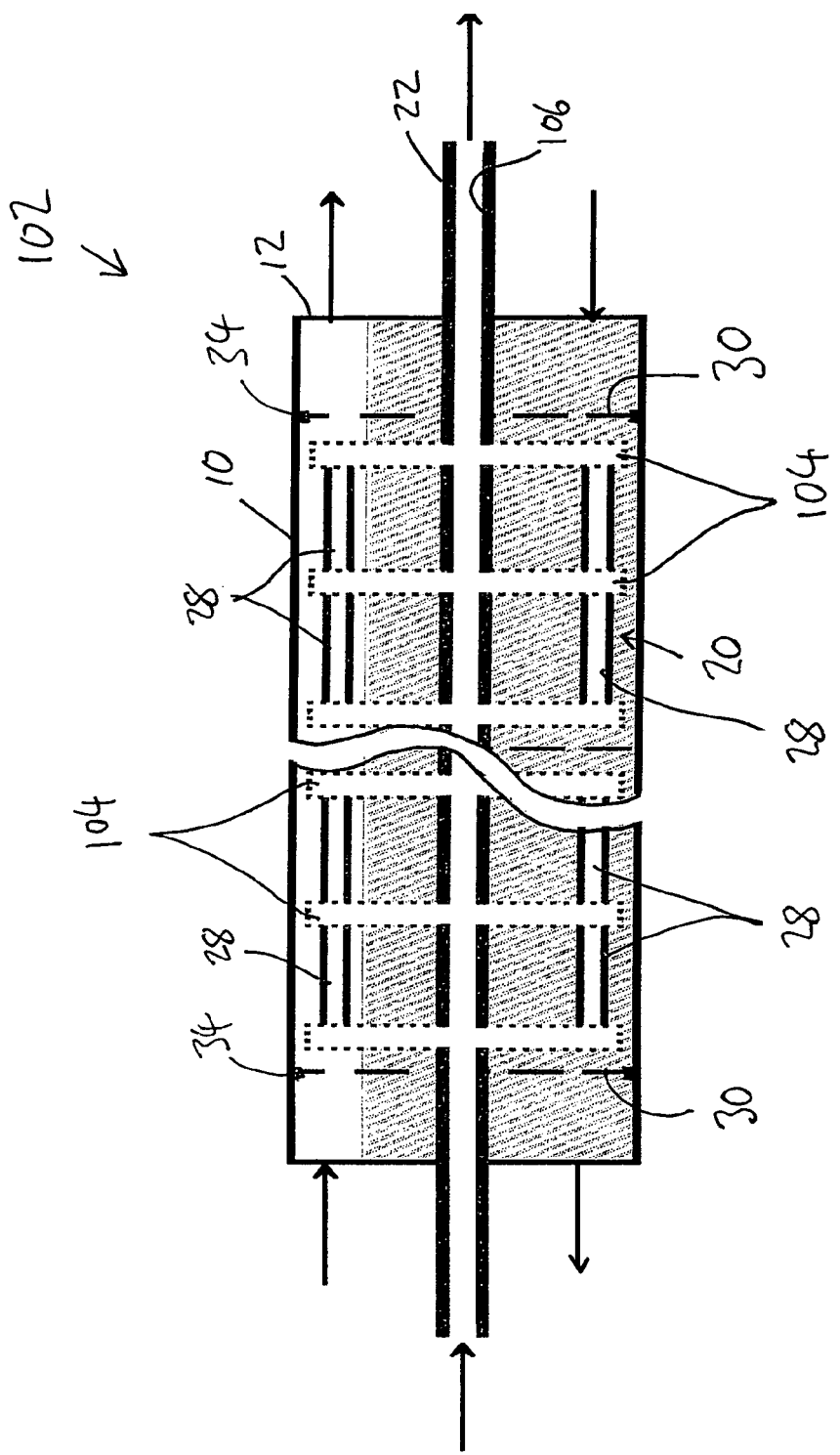

A still further alternative mode of operation of the reactor assembly shown in FIG. 6 is represented in FIG. 10, which is a cross-sectional view corresponding that that of FIG. 7 but operating in the following manner. An aqueous liquid medium containing microorganisms is fed into the reactor vessel as described hereinbefore and occupies a first region 70 of the reactor vessel. A gaseous stream to be treated, for example a flue gas, is fed into the reactor vessel as described above and occupies a second region 72 of the reactor vessel, above the first region 70. A gas exchange solvent, such as a perfluorinated hydrocarbon, is introduced into the reactor vessel and occupies a third region 74 of the reactor vessel. As the density of the gas exchange solvent is greater than that of the aqueous microorganism-containing medium, the gas exchange solvent occupies a region below the aqueous medium. Before being fed into the reactor vessel, the gas exchange solvent may be contacted with a fluid stream to be processed, so as to remove one or more gaseous components therefrom, in particular to remove carbon dioxide from a gaseous stream, such as a flue gas or the like. Suitable apparatus and systems for contacting a gas exchange solvent with a gas stream are known in the art. The stream of gas exchange solvent containing the gas dissolved therein is then fed into the reactor vessel. A solvent stream, such a dodecane, is introduced into the reactor vessel and occupies a fourth region 76 between the first and second regions, due to its density relative to the components of the other streams. The solvent may be selected to preferentially remove components from the reactor vessel, in particular the products of the metabolism of the microorganisms, such as non-polar hydrocarbons and the like.

Contact between the microorganisms in the liquid medium, gases in the gas stream, the solvent and the gas exchange solvent is promoted in a manner analogous to the operation described above, with the bubbles 78 of the gas and the bubbles 80 of the solvent captured by the troughs passing upwards through the microorganism-containing liquid medium and the bubbles 82 of the gas exchange solvent captured by the troughs passing downwards through the microorganism-containing medium, as shown in FIG. 10.

Gases, such as carbon dioxide, are consumed from the gas stream and the gas exchange solvent, if present, by the microorganisms. In addition, gaseous products of the microorganism metabolism, such as oxygen, are absorbed by the gas exchange solvent and leave the reactor vessel in the gas exchange solvent stream or pass into the gas stream, for subsequent recovery, as required. Depending upon the selection of components in the solvent phase, one or more further components, including metabolic products of the microorganisms, may be absorbed and removed by way of the solvent phase. Finally, gaseous components entering the reactor vessel in the gaseous stream but not consumed by the microorganisms may be recovered and removed by the action of the gas exchange solvent. This mode of operation is again particularly advantageous as it allows carbon capture from streams such as flue gases and the like to continue during times of darkness or low light levels, when the conditions are not suitable for photosynthesis by the microorganisms. At such times, the capture of carbon in the form of carbon-containing gases is effected solely by the removal of such gases from the gaseous stream by the gas exchange solvent.

Again, the flow of the liquid microorganism-containing medium, the gas stream, the solvent phase and the gas exchange solvent may be either co-current or counter-current through the reactor vessel, as required for optimum operation.

The solvent and gas exchange solvent may be regenerated after leaving the reactor assembly by removing the components dissolved therein in known manner using known technology and recycled to the inlet of the reactor assembly.

Temperature regulation within the reactor vessel may be achieved in a variety of ways. For example, cooling of the reactor vessel may be achieved by sprinkling a coolant, most suitably water, on the exterior surface of the reactor, whereby heat is removed by evaporative cooling. Heating of the contents of the reactor vessel may be achieved by heating one or more of the fluid streams before being fed to the reactor assembly or by using a hot fluid stream, such as a hot flue gas stream. Heat transfer within the reactor vessel may also be provided by using a hollow shaft 22, through which a heat transfer medium may be pumped to either heat or cool the contents of the reactor vessel. A combination of two or more of the aforementioned techniques may be employed, as appropriate.

Turning to FIG. 11, there is shown a longitudinal representation of an alternative arrangement of the reactor assembly of FIG. 6, generally indicated as 102. The components of the reactor assembly shown in FIG. 11 in common with those of the assembly of FIG. 6 are indicated using the same reference numerals and are as described as set out above. In the assembly 102 of FIG. 11, the rotor assembly is provided with rotor plates 104 having a hollow construction and formed from a porous material having pores that are sufficiently small to prevent the passage of microorganisms or biomass therethrough. Alternatively, the rotor plates 104 are provided with openings with openings covered with a filter material, again having a pore size sufficiently small to prevent the passage of microorganisms or biomass therethrough. The hollow interior of the rotor plates 104 provides a passage for the flow of fluids into a longitudinal bore 106 extending within the shaft 22. In operation, components in the fluid media within the reactor vessel are continuously removed through the rotor plates 104 and the shaft 22, while leaving the microorganisms retained within the reactor vessel 10. In this way, the build up of the products of the metabolism of the microorganisms that may inhibit the continued growth of the microorganisms is prevented. For example, dinoflagelllates excrete neurotoxins into their growth media, which have an inhibiting effect on the growth of the microorganisms, eventually leading to death. The reactor assembly of FIG. 11 allows the neurotoxins to be continuously removed, enhancing the viability of the dinoflagellates and providing for enhanced production of the neurotoxin component.

Referring to FIGS. 12a to 12c, there are shown pond bioreactors embodying principles of the reactor of the present invention. Thus, in FIG. 12a there is shown a pond, generally indicated as 200, having side walls 202 and a generally flat floor 204. A plurality of rotor assemblies 206 are provided for rotation within the pond. The rotor assemblies 206 are constructed as described hereinbefore and operate in analogous manner in the pond, providing for a low shear agitation of the liquid microorganism-containing medium contained within the pond. The pond shown in FIG. 12a is open. A closed pond 210 is shown in FIG. 12b having a similar construction to the pond of FIG. 12a, but provided with a transparent cover 212. The pond 220 shown in FIG. 12c is of a similar construction to that of FIG. 12b, but with the floor of the pond being formed with longitudinal recesses 222, within each of which a rotor assembly is mounted for rotation.

Figure 13:
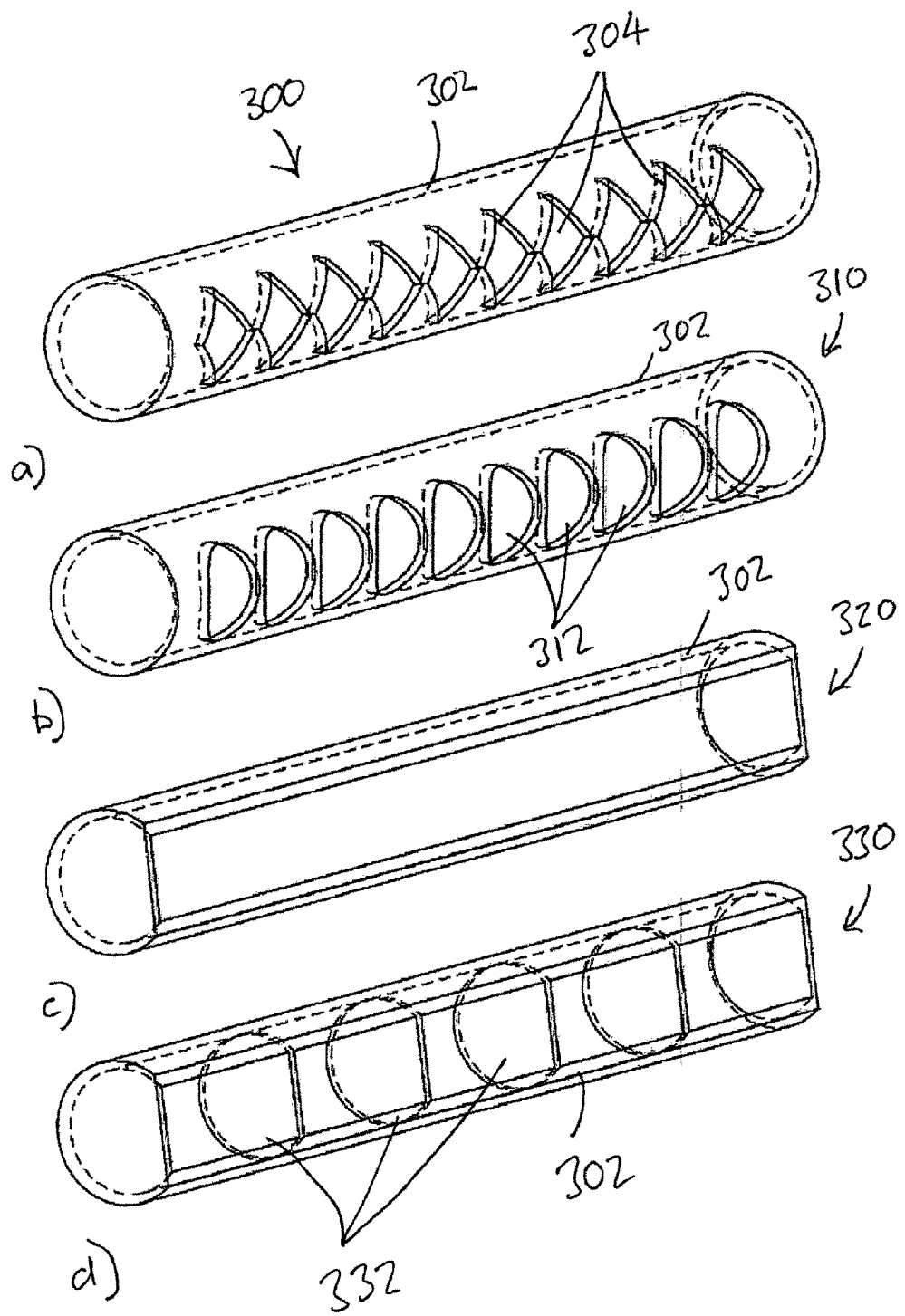
FIGS. 13a to 13d are perspective views of alternative trough configurations for use as impellers in the reactor assembly of the present invention.

Referring to FIGS. 13a to 13d, there are shown alternative arrangements of impeller for use in the reactor assembly of the present invention. Thus, in FIG. 13a there is shown an impeller generally indicated as 300 comprising an open, generally cylindrical trough 302. Within the trough 302 are disposed generally triangular baffles 304 spaced along the trough. The size, shape and spacing of the baffles 304 are selected to provide the required droplet/bubble size for the fluid streams present in the reactor assembly. An alternative impeller arrangement 310 is shown in FIG. 13b, comprising a trough 302 of the same configuration as FIG. 13a, but provided with a plurality of generally semicircular baffles 312. The size and spacing of the baffles 312 is selected to provide the desired droplet/bubble size in the reactor system. An impeller assembly 320 comprising a plain trough 302 is shown in FIG. 13c. Finally, FIG. 13d shows an impeller assembly 330 having a similar trough 302, provided with a plurality of substantially circular baffles 332. Again, the size, number and spacing of the baffles 332 may be varied to provide the required droplet/bubble size in the reactor assembly.

The invention claimed is:

1. An apparatus for contacting a fluid stream with microorganisms, the apparatus comprising:
 a housing having a contacting chamber therein defined by a wall of the housing;
 a first inlet for the fluid stream to be treated;
 a first outlet for removing a liquid culture medium stream containing microorganisms;
 a rotor assembly comprising an impeller moveable within the contacting chamber to promote contact between the fluid stream being treated and the liquid culture medium within the contacting chamber, the impeller comprising an elongate scoop or bucket; wherein the rotor assembly further comprises an array of light emitting devices to provide a source of artificial light within the housing;
 wherein at a least a portion of the wall of the housing defining the contacting chamber is transparent to light;
 wherein, in use, the contact chamber has a first region occupied by fluid from the fluid stream to be processed and a second region occupied by the liquid medium containing microorganisms, the inlet directing fluid to be processed into the first region of the contact chamber;
 the impeller moving through both the first and second regions of the contact chamber;

the apparatus further comprising:
low density or floating solid materials to clean the inner surface of the housing; and
a system for applying a potential difference across the impellor of the rotor assembly.

2. The apparatus according to claim 1, wherein the housing is generally cylindrical and has a wall defining a generally cylindrical contacting chamber.

3. The apparatus according to claim 1, wherein the housing is arranged with its longitudinal axis generally horizontal.

4. The apparatus according to claim 1, wherein the housing comprises a plurality of contacting chambers, each contacting chamber having an impeller disposed and moveable therein.

5. The apparatus according to claim 1, wherein substantially all of the housing is transparent to light.

6. The apparatus according to claim 1, wherein the rotor assembly is arranged to impart low shear to the fluid media when moving the impeller within the contacting chamber.

7. The apparatus according to claim 1, wherein the impeller is elongate and extends substantially the entire length of the contacting chamber in which it is disposed.

8. The apparatus according to claim 1, wherein the rotor assembly comprises a shaft extending longitudinally within the contacting chamber, each impeller being supported on the shaft, wherein the shaft is hollow, providing a passage for the supply of a heat transfer fluid.

9. The apparatus according to claim 1, wherein the housing comprises a plurality of contacting chambers, a single rotor assembly being provided to move one or more impellers disposed within each contacting chamber.

10. The apparatus according to claim 1, further comprising a wiper assembly for removing deposited material on the transparent portion of the housing.

11. The apparatus according to claim 10, wherein the wiper assembly is moveable in a reciprocating manner.

* * * * *